(12) United States Patent
Empedocles et al.

(10) Patent No.: US 6,759,235 B2
(45) Date of Patent: Jul. 6, 2004

(54) TWO-DIMENSIONAL SPECTRAL IMAGING SYSTEM

(75) Inventors: Stephen A. Empedocles, Mountain View, CA (US); Andrew R. Watson, Belmont, CA (US)

(73) Assignee: Quantum Dot Corporation, Hayward, CA (US)

( * ) Notice: Subject to any disclaimer, the term of this patent is extended or adjusted under 35 U.S.C. 154(b) by 0 days.

(21) Appl. No.: 09/827,076

(22) Filed: Apr. 5, 2001

(65) Prior Publication Data

US 2002/0031783 A1 Mar. 14, 2002

Related U.S. Application Data

(60) Provisional application No. 60/195,520, filed on Apr. 6, 2000.

(51) Int. Cl.[7] .......................... C12M 1/34; G01N 21/76
(52) U.S. Cl. .................. 435/288.7; 435/287.1; 435/287.2; 435/6; 435/7.92; 435/7.93; 436/164; 436/172
(58) Field of Search .................. 435/6, 7, 92, 7.93, 435/287.1, 287.2, 287.9, 288.7; 422/82.08; 436/164, 172

(56) References Cited

U.S. PATENT DOCUMENTS

| | | | |
|---|---|---|---|
| 5,079,169 A | | 1/1992 | Chu et al. |
| 5,377,003 A | * | 12/1994 | Lewis et al. ................ 356/300 |
| 5,460,831 A | | 10/1995 | Kossovsky et al. |
| 5,495,334 A | * | 2/1996 | Nagoshi et al. ............. 356/456 |
| 5,512,745 A | | 4/1996 | Finer et al. |
| 5,543,158 A | | 8/1996 | Gref et al. |
| 5,620,857 A | | 4/1997 | Weetall et al. |
| 5,665,582 A | | 9/1997 | Kausch et al. |
| 5,939,021 A | | 8/1999 | Hansen et al. |
| 5,990,479 A | | 11/1999 | Weiss et al. |
| 6,108,463 A | * | 8/2000 | Herron et al. ................ 385/12 |
| 6,207,392 B1 | | 3/2001 | Weiss et al. |
| 6,225,198 B1 | | 5/2001 | Alivisatos et al. |
| 6,235,540 B1 | | 5/2001 | Siiman et al. |
| 6,322,901 B1 | * | 11/2001 | Bawendi et al. ............. 428/403 |
| 6,326,144 B1 | * | 12/2001 | Bawendi et al. ............... 435/8 |
| 6,492,125 B2 | * | 12/2002 | Kauvar et al. ............... 435/7.1 |
| 2002/0022273 A1 | * | 2/2002 | Empedocles et al. ....... 436/171 |

FOREIGN PATENT DOCUMENTS

| | | | |
|---|---|---|---|
| EP | 0990903 | 4/2000 | |
| WO | WO 99/26299 | 5/1999 | |
| WO | WO 99/50916 | * 10/1999 | ........... H01L/33/00 |
| WO | WO 00/68692 | 11/2000 | |

OTHER PUBLICATIONS

Brunchez et al., "Semiconductor Nanocrystals as Fluorescent Biological Labels", Science, vol. 281, 2013–2016, 1998.*

* cited by examiner

*Primary Examiner*—Padmashri Ponnaluri
*Assistant Examiner*—My-Chau T. Tran
(74) *Attorney, Agent, or Firm*—Townsend & Townsend & Crew LLP; Mark D. Barrish, Esq.

(57) ABSTRACT

Improved devices, systems, and methods for sensing and/or identifying signals from within a signal detection region are well-suited for identification of spectral codes. Large numbers of independently identifiable spectral codes can be generated by quite small bodies, and a plurality of such bodies or probes may be present within a detection region. Simultaneously imaging of identifiable spectra from throughout the detection region allows the probes to be identified. As the identifiable spectra can be treated as being generated from a point source within a much larger detection field, a prism, diffractive grading, holographic transmissive grading, or the like can spectrally disperse the images of the labels across a sensor surface. A CCD can identify the relative wavelengths of signals making up the spectra. Absolute signal wavelengths may be identified by determining positions of the labels, by an internal wavelength reference within the spectra, or the like.

36 Claims, 10 Drawing Sheets

TWO-DIMENSIONAL SPECTRAL IMAGING SYSTEM

CROSS-REFERENCES TO RELATED APPLICATIONS

The application claims the benefit of priority from co-pending U.S. Provisional Patent Application No. 60/195,520 entitled "Method for Encoding Materials with Semiconductor Nanocrystals, Compositions Made Thereby, and Devices for Detection and Decoding Thereof," filed Apr. 6, 2000, the full disclosure of which is incorporated herein by reference.

The subject matter of the present application is related to the following co-pending patent applications, the disclosures of which are also incorporated herein by reference: U.S. patent application Ser. No. 09/160,458 filed Sep. 24, 1998 and entitled, "Inventory Control"; U.S. patent application Ser. No. 09/397,432 filed Sep. 17, 1999, and also entitled "Inventory Control"; PCT Patent Application No. WO 99/50916 as published on Apr. 1, 1999, entitled "Quantum Dot White and Colored Light Emitting Diodes"; and U.S. patent application Ser. No. 09/259,982 filed Mar. 1, 1999, and entitled "Semiconductor Nanocrystal Probes for Biological Applications and Process for Making and Using Such Probes".

BACKGROUND OF THE INVENTION

The present invention generally provides devices, compositions of matter, kits, systems and methods for detecting and identifying a plurality of signals from within a signal area. In a particular embodiment, the invention provides systems and methods for detecting and identifying a plurality of spectral barcodes from throughout a sensing area, especially for identifying and/or tracking inventories of elements, for high-throughput assay systems, and the like. The invention will often use labels which emit identifiable spectra that include a number of discreet signals having measurable wavelengths and/or intensities.

Tracking the locations and/or identities of a large number of items can be challenging in many settings. Barcode technology in general, and the Universal Product Code in particular, has provided huge benefits for tracking a variety of objects. Barcode technologies often use a linear array of elements printed either directly on an object or on labels which may be affixed to the object. These barcode elements often comprise bars and spaces, with the bars having varying widths to represent strings of binary ones, and the spaces between the bars having varying widths to represent strings of binary zeros.

Barcodes can be detected optically using devices such as scanning laser beams or handheld wands. Similar barcode schemes can be implemented in magnetic media. The scanning systems often electro-optically decode the label to determine multiple alphanumerical characters that are intended to be descriptive of (or otherwise identify) the article or its character. These barcodes are often presented in digital form as an input to a data processing system, for example, for use in point-of-sale processing, inventory control, and the like.

Barcode techniques such as the Universal Product Code have gained wide acceptance, and a variety of higher density alternatives have been proposed. Unfortunately, these standard barcodes are often unsuitable for labeling many "libraries" or groupings of elements. For example, small items such as jewelry or minute electrical components may lack sufficient surface area for convenient attachment of the barcode. Similarly, emerging technologies such as combinatorial chemistry, genomics research, microfluidics, micromachines, and other nanoscale technologies do not appear well-suited for supporting known, relatively large-scale barcode labels. In these and other developing fields, it is often desirable to make use of large numbers of fluids, and identifying and tracking the movements of such fluids using existing barcodes is particularly problematic. While a few chemical encoding systems for chemicals and fluids have been proposed, reliable and accurate labeling of large numbers of small and/or fluid elements remains a challenge.

Small scale and fluid labeling capabilities have recently advanced radically with the suggested application of semiconductor nanocrystals (also known as Quantum Dot™ particles), as detailed in U.S. patent application Ser. No. 09/397,432, the full disclosure of which is incorporated herein by reference. Semiconductor nanocrystals are microscopic particles having size-dependent optical and/or electrical properties. As the band gap energy of such semiconductor nanocrystals vary with a size, coating and/or material of the crystal, populations of these crystals can be produced having a variety of spectral emission characteristics. Furthermore, the intensity of the emission of a particular wavelength can be varied, thereby enabling the use of a variety of encoding schemes. A spectral label defined by a combination of semiconductor nanocrystals having differing emission signals can be identified from the characteristics of the spectrum emitted by the label when the semiconductor nanocrystals are energized.

While semiconductor nanocrystal-based spectral labeling schemes represent a significant advancement for tracking and identifying many elements of interest, still further improvements would be desirable. In general, it would be beneficial to provide improved techniques for sensing or reading these new spectral labels. It would be particularly beneficial to provide improved techniques for applying these labeling and tracking technologies to high-throughput assay systems now being developed.

Multiplexed assay formats would be highly desirable for improved throughput capability, and to match the demands that combinatorial chemistry is putting on established discovery and validation systems for pharmaceuticals. For example, simultaneous elucidation of complex protein patterns may allow detection of rare events or conditions, such as cancer. In addition, the ever-expanding repertoire of genomic information would benefit from very efficient, parallel and inexpensive assay formats. Desirable multiplexed assay characteristics include ease of use, reliability of results, a high-throughput format, and extremely fast and inexpensive assay development and execution.

A number of known assay formats may be employed for high-throughput testing. Each of these formats has limitations, however. By far the most dominant high-throughput technique is based on the separation of different assays into different regions of space. The 96-well plate format is the workhorse in this arena.

In 96-well plate assays, the individual wells (which are isolated from each other by walls) are often charged with different components, and the assay is performed and then the assay result in each well measured. The information about which assay is being run is carried with the well number, or the position on the plate, and the result at the given position determines which assays are positive. These assays can be based on chemiluminescence, scintillation, fluorescence, scattering, or absorbance/colorimetric measurements, and the details of the detection scheme depend on the reaction being assayed.

Multi-well assays have been reduced in size to enhance throughput, for example, to accommodate 384 or 1536 wells per plate. Unfortunately, the fluid delivery and evaporation of the assay solution at this scale are significantly more confounding to the assays. High-throughput formats based on multi-well arraying often rely on complex robotics and fluid dispensing systems to function optimally. The dispensing of the appropriate solutions to the appropriate bins on the plate poses a challenge from both an efficiency and a contamination standpoint, and pains must be taken to optimize the fluidics for both properties. Furthermore, the throughput is ultimately limited by the number of wells that one can put adjacent on a plate, and the volume of each well. Arbitrarily small wells have arbitrarily small volumes, resulting in a signal that scales with the volume, shrinking proportionally with the cube of the radius. The spatial isolation of each well, and thereby each assay, has been much more common than running multiple assays in a single well. Such single-well multiplexing techniques are not widely used, due in large part to the difficulty in "demultiplexing" or resolving the results of the different assays in a single well.

For even higher throughput genomic and genetic analysis techniques, positional array technology has been shrunk to microscopic scales, often using high-density oligonucleotide arrays. Over a 1-cm square of glass, tens to hundreds of thousands of different nucleotides can be written in, for example, 25-$\mu$m spots, which are well resolved from each other. On this planar test structure or "chip," which is emblazoned with an alignment grid, a particular spot's x,y position determines which oligonucleotide is present at that spot. Typically fluorescently-labeled amplified DNA is added to the array, hybridized and is then detected using fluorescence-based techniques. Although this is a very powerful technique for assaying a large number of genetic markers simultaneously, the cost is still very high, and the flexibility of this assay is extremely limited.

Once a chip is made with particular DNA sequences at particular locations, they are fixed and the addition thereto of new markers comes at a very high price. The extremely small feature size, and the highly parallel assay format, comes at the cost of the flexibility inherent in a common platform system, such as the 96-well plates. In addition, this assay is ultimately performed at the surface of the chip, and the results depend on the kinetics of the hybridization to the surface, a process that is negatively influenced by steric issues, mixing issues, and diffusion issues. In fact, small microarray chips are not particularly suited to the detection of rare events, as the diffusion of the solution over the chip may not be sufficiently thorough. In order to perform the hybridizations to the microarray chips more efficiently, a dedicated fluidics workstation can be used to pump the solution over the surface of the chip repeatedly; such instruments add cost and time to execution of the assay.

The use of spectral barcodes holds great promise for enhancing the throughput of assays, as described in an application entitled "Semiconductor Nanocrystal Probes for Biological Applications and Process for Making and Using such Probes," U.S. Application Ser. No. 09/259,982 filed Mar. 1, 1999, the full disclosure of which is incorporated herein by reference. Multiplexed assays may be performed using a number of probes which include both a spectral label (often in the form of several semiconductor nanocrystals) and one or more moieties. The moieties may be capable of selectively bonding to one or more detectable substances within a sample fluid, while the spectral labels can be used to identify the probe within the fluid (and hence the associated moiety). As the individual probes can be quite small, and as the number of barcodes which can be independently identified can be quite large, large numbers of individual assays might be performed within a single fluid sample by including a large number of differing probes. These probes may take the form of quite small beads, with each bead optionally including a spectral label, a moiety, and a bead body or matrix, often in the form of a polymer.

Together with the substantial advantages provided by highly multiplexed, spectrally-encoded assay bead systems, there will be significant challenges in implementing these techniques. In particular, determining multiplexed assay results might be quite challenging. While the reaction times and accuracy of the spectral labels can be quite advantageous, it can be challenging to accurately read each spectral barcode and/or assay result from the hundreds, and in many cases thousands, of beads within a highly multiplexed bead assay system. Similarly, while spectral coding in general allows labeling and/or identification of a large number of elements, interpreting the spectral codes can be quite challenging when the individual label structures are small, and when many labels are located near each other.

In light of the above, it would generally be desirable to provide improved systems and methods for detecting and identifying signals. It would be particularly beneficial if these improved techniques facilitated the identification of each spectral code from among a plurality of spectral barcodes in a given region. To take advantage of the potential capabilities of spectral coding of minute probes and other structures, it would be highly desirable if these enhanced techniques allowed detection and/or identification of large numbers of spectral codes or other signals (such as assay marker signals) in a highly time efficient manner.

SUMMARY OF THE INVENTION

The present invention generally provides improved devices, systems, and methods for sensing and/or identifying signals. The techniques of the present invention are particularly well-suited for identification of labels which generate spectral codes. Large numbers of independently identifiable spectral codes can be generated by quite small bodies having such labels, and a plurality of such bodies or probes may be present within a detection region. In some embodiments, the invention allows simultaneously imaging of identifiable spectra from throughout the detection region. This simultaneous imaging allows the labels (and hence, the associated probes, assay results, and the like) to be identified. A wavelength dispersive element (for example, a prism, diffractive grating, holographic transmissive grating, or the like) can simultaneously spectrally disperse the images of the labels across a sensor surface. A two-dimensional areal light sensor (such as a Charge-Coupled Device or "CCD") can substantially simultaneously sense the relative wavelengths of signals making up the spectra. Taking advantage of a very small label size, the identifiable spectra can be treated as being generated from point-sources within a large detection field, thereby acting as their own "slit" in this spectroscopic instrument. Absolute signal wavelengths may be identified by determining positions of the labels, using an internal wavelength reference within the spectra, and/or the like.

Spectral labels may be used with other markers generating signals that differ significantly from the identifiable spectra from the labels. For example, spectrally encoded beads may be used within parallel assay systems by generating assay signals in addition to the label spectra. These assay signals may accurately and reliably indicate the results of the assay, but these signals may be significantly lower in intensity than the spectral label. Hence, the present invention also provides techniques for identifying signals of widely varying strengths. These techniques often involve simultaneously sensing lower intensity signals using a relatively long integration time with areal imaging. Higher intensity signals can be sequentially sensed, often using a scanning system. This dual sensing system enhances the overall efficiency of signal detection and interpretation by allowing a relatively long signal integration time for the lower intensity signals, while the higher intensity signals are quickly scanned with a shorter integration time. In some embodiments, a plurality of excitation energies may be directed toward the signal generators, with at least one of the excitation energies selectively producing the lower energy signals. Such techniques are particularly well-suited to take advantage of the capabilities of semiconductor nanocrystals, which can accurately generate detectable signals from minute bodies, and which can be selectively energized by appropriate excitation sources.

In a first aspect, the invention provides a system comprising a plurality of labels generating identifiable spectra in response to excitation energy. A detector simultaneously images at least some of the spectra for identification of the labels.

In many embodiments, at least some of the spectra will comprise a plurality of detectable signals defining a plurality of wavelengths. Label markers may generate these different label signals, so that the labels can comprise a plurality of label markers. The wavelengths from the spectra can be intermingled. Preferably, the labels will comprise at least one semiconductor nanocrystal. More typically, each label will comprise at least one population of semiconductor nanocrystals, with each semiconductor nanocrystal of each population generating a signal having an associated population wavelength in response to the excitation energy. In many embodiments, the labels will comprise a plurality of populations supported by a matrix.

In some embodiments, at least one probe body will include a label and an associated assay indicator marker. The indicator markers generate indicator signals in response to an interaction between the probe body and an associated test substance, thereby indicating results of an assay.

The labels may be distributed across a two-dimensional sensing field. The detector will often include a wavelength dispersive element and a sensor, and each label will preferably be sufficiently smaller than the surrounding sensing field to allow the spectra to be wavelength-dispersed by the wavelength dispersive element without excessive overlap of the dispersed spectra upon the sensor. The dispersed spectra can often be analyzed as being generated from discrete point-light sources. By using discrete point source spectral labels, the system avoids any need for slit apertures or the like, as generally found on linear spectrometers and other spectral dispersion systems. In other words, the small labels can act as their own slits. This also allows the detector to admit signals from throughout a two-dimensional sensing field.

The wavelength dispersive element is usually disposed between the sensing field and the light sensor. The sensor simultaneously senses the spectra from the plurality of labels. An open optical path often extends from the sensing field to the wavelength dispersive element, and from the wavelength dispersive element to the sensor, with optics typically imaging the sensing field on the sensor. The sensor will typically comprise an areal sensor (such as CCD), and the open optical path will have an open cross-section with significant first and second open orthogonal dimensions, in contrast to the slit or point apertures often used in dispersive systems. The wavelength dispersive element may comprise a prism, a dispersive reflective grating, a holographic transmission grating, or the like.

In many embodiments, a spatial positioner provides label positions within the sensor field. The detector will often sense relative spectral data, while an analyzer coupled to the label positioner and the detector can derive absolute wavelengths of the spectra in response to both the relative spectral data and the indicated label positions. In some embodiments, a beam splitter may optically couple the label positioner with the sensing field along a positioning optical path, and may also couple the detector with the sensor field along a spectral optical path, so that at least a portion of the positioning and spectral optical paths make use of common optical elements. The beam splitter may direct most of the energy from the sensing field toward the detector for relative spectral information, and a minority of the energy from the sensing field toward a positioning image. In some embodiments, a beam splitter may direct a portion of an image from the sensing field to a first dispersion member so as to distribute the spectra along a first axis relative to the sensing field, and a second portion of the image to a second dispersion member so as to distribute the spectra along a second axis, the second axis being at an angle to the first axis relative to the sensing field for resolving spectral ambiguities from any overlapping wavelengths along the first axis. Similar ambiguity resolution techniques may sequentially disperse the spectra along differing axes.

At least some of the spectra will often comprise a plurality of signals. The detector may include means for distributing these signals across a sensor in response to wavelengths of the signals, and in response to positions of the labels in the sensor fields. The distributing means may be disposed between the sensing field and the sensor. The system may also include means for determining positions of the labels within the sensing field, with a spectral analyzer coupled to the positioning means and the sensor so that the analyzer can determine the spectra. The positioning means may optionally comprise an areal sensor and a beam splitter, a calibration reference signal within some or all of the spectra, or the like.

In another aspect, the invention provides a system comprising a plurality of labels distributed across a two-dimensional sensing field. The labels generate spectra in response to excitation energy. A wavelength dispersive element is disposed in an open optical path of the spectra from the two-dimensional sensing field. A sensor is disposed in the path from the wavelength dispersive element. A label positioning system is coupled to the labels and an analyzer is coupled to the sensor for identifying the labels in response to the sensed spectral information.

In another aspect, the invention provides a method comprising generating spectra from a plurality of labels. The spectra are sensed with a sensor by simultaneously imaging the labels on the sensor, and the labels are identified in response to the sensed spectra.

In many embodiments, the labels will be movably disposed within a two-dimensional sensing field while the spectra are sensed. The positions of the labels may be determined when the spectra are sensed by the sensor, and the labels may be identified in response to the label positions (as well as using the data from the sensor). The spectra from the labels will often be dispersed. In some embodiments, the spectra will be dispersed along a second dispersion axis at an angle to a first dispersion axis so as to resolve ambiguity from spectral overlap.

In another aspect, the invention provides a method for identifying signals of differing strengths. The method comprises generating a plurality of signals in response to excitation energy. The signals include higher intensity signals and lower intensity signals. The lower intensity signals are sensed by simultaneously imaging the signals. At least some of the higher intensity signals are sequentially sensed.

In many embodiments, the lower intensity signals will be sensed by imaging a sensing field for a first integration time. The higher intensity signals may be sequentially sensed by imaging a portion of the sensing field for a second integration time, the second integration time being shorter than the first integration time. Optionally, the higher intensity signals may be filtered from the simultaneous image. This is facilitated where the higher intensity signals have wavelengths that are different than wavelengths of the lower intensity signals, as wavelength filtering may be employed to avoid saturation of the image.

The higher intensity signals may be sequentially sensed by scanning labels which generate the signals. The labels generating the higher intensity signals may be spatially intermingled with markers generating the lower intensity signals. Scanning may comprise scanning an aperture relative to the labels, such as a slit, a pinhole aperture, or the like. In some embodiments, scanning may be performed by scanning an excitation energy over a portion of the sensing field.

In some embodiments, the excitation energy may comprise a first energy for exciting the higher energy markers of the labels to generate the high energy signals, and a second energy for generating the lower energy signals. The second energy may selectively excite the low energy markers.

The higher intensity signals of the labels may be generated by label markers and can define an identifiable spectral code. The low intensity signals may be generated by assay markers and can indicate results of a plurality of assays, with each assay having an associated spectral code. The markers may be supported by probe bodies to define probes. Each probe can include a plurality of label markers, which together define a label (to generate the spectral code), and at least one associated assay marker (to indicate results of an associated assay). The results of each assay may be determined by identifying each label, and by correlating the label with an associated assay marker signal.

In another aspect, the invention provides a method for acquiring signals. The method comprises generating a first plurality of signals from a first plurality of markers in response to a first excitation energy. A second plurality of signals are generated from a second plurality of markers in response to a second excitation energy. The first and second markers are intermingled. Intensities of the first signals are tuned relative to intensities of the second signals by selecting a characteristic of at least one of the first and second excitation energies. The tuned first and second signals are simultaneously imaged on a sensor.

Typically, at least one of the markers will comprise a semiconductor nanocrystal. Preferably, the first energy will selectively energize the first plurality of markers. The intensities will be tuned so that the signals are within an acceptable intensity range of the sensor during a common integration time by varying an intensity of at least one of the first and second excitation energies.

In yet another aspect, the invention provides a high-throughput assay method comprising performing a plurality of assays, and generating assay signals with assay markers to indicate the results of the assays. The assay markers are simultaneously area imaged, and spectral codes associated with each assay marker are generated. The assay results are interpreted by identifying the spectral code and assay markers, and by correlating each spectral code with an associated assay marker signal.

In another aspect, the invention provides a system for detecting spectral information. Spectral information includes higher intensity signals and lower intensity signals. The signals are generated within a two-dimensional field. The systems comprises a detector optically couplable with the two-dimensional field for simultaneous imaging of the low intensity signals. A scanner has an aperture movable relative to the two-dimensional field for sequential imaging of the higher intensity signals.

In yet another aspect, the invention provides a system comprising a plurality of labels generating identifiable spectra in response to excitation energy. Other markers are intermingled with the labels. The other markers generate other signals, with the other signals being weaker than the spectra. A scanner has an aperture movable relative to the labels for identifying the spectra. A detector is optically coupled to the plurality of other markers for simultaneously imaging the other signals.

Typically, groups of the markers will be held together by a probe matrix so as to define a plurality of probes, with each probe including at least one label and at least one associated other marker. This allows each probe to indicate results of an associated assay via the identifiable spectra of the label. A processor coupled to the scanner and to the detector can determine the results of the assay in response to the spectra as sensed by the scanner, and in response to the associated assay markers as sensed by the detector. An integration time of the detector can be longer than an integration time of the scanner for the spectra without overly delaying the identification time, as the other markers (or assay markers) are simultaneously imaged throughout the sensing field.

In yet another aspect, the invention provides a high-throughput assay system comprising a fluid with an excitation energy source transmitting excitation energy toward the fluid. A plurality of assay probes are disposed in the fluid. Each probe has a spectral label. The spectral labels generate identifiable spectral codes in response to the excitation energy. The probes generate assay signals in response to assay results. A scanner moves a sensing region relative to the fluid (and/or at least one of the fluid and fluid holder relative to the sensing region) for identification of the probes from the spectral codes. The two-dimensional imaging system images the assay markers from the probes throughout the two-dimensional sensing field simultaneously.

In yet another aspect, the invention provides a high-throughput assay system comprising a fluid and a first excitation energy source transmitting a first excitation energy toward the fluid. The second excitation energy source transmits a second excitation energy toward the fluid. A plurality of assay probes are disposed in the fluid. Each probe has a spectral label, and assay markers in the fluid are associated with the probes. The assay markers transmit an assay signal in response to assay results, and in response to the second excitation energy. A first excitation energy selectively energizes the spectral labels so that the spectral labels transmit identifiable spectral codes. A sensing system senses the assay signals and the spectral codes. The sensing system has an intensity range. Intensities of the first and second excitation sources are selected so that the assay signals and the spectral codes are within the intensity range, often at the same integration time.

In yet another aspect, the invention provides a fluid-flow assay system comprising a fluid and a probe movably disposed within the fluid. The probe has a label to generate an identifiable spectra and an assay marker to generate an assay signal in response to interaction between the probe and a detectable substance. A probe reader senses the spectra and signal when the probe and fluid flow through a sensing region to determine an assay result.

Typically, a plurality of differing probes will flow through the sensing region. The probe reader will determine results of a plurality of different assays by identifying the probes from their associated spectra, and by correlating the assay signals from the probes with the associated assays of the identified probes. In the exemplary embodiment, the fluid (and the probes) flow across a slit aperture within a thin, flat channel so that the distance between the probes and reader is substantially uniform. This facilitates imaging of the probes within the sensing region.

In yet another aspect, the invention provides a fluid-flow assay method comprising moving a probe by flowing a fluid. A spectra from the moving probe is sensed while the probe acts as its own aperture by dispersing the image, and results of an assay are determined by identifying the probe from the spectra. Once again, such methods are particularly useful for multiplexed assays, as a plurality of differing probes can be identified and their assay results correlated.

DESCRIPTION OF THE SPECIFIC EMBODIMENTS

The present invention generally provides improved devices, systems, methods, compositions of matter, kits, and the like for sensing and interpreting spectral information. The invention is particularly well-suited to take advantage of new compositions of matter which can generate signals at specific wavelengths in response to excitation energy. A particularly advantageous signal generation structure for use of the present invention is the semiconductor nanocrystal. Other useful signaling structures may also take advantage of the improvements provided by the present invention, including conventional fluorescent dyes, radiated elements and compounds, and the like.

The invention can allow efficient sensing and/or identification of a large number of spectral codes, particularly when each code includes multiple signals. The invention may also enhance the reliability and accuracy with which such codes are read, and may thereby enable the use of large numbers of spectral codes within a relatively small region. Hence, the techniques of the present invention will find advantageous applications within highly multiplexed assays, inventory control in which a large number of small and/or fluid elements are intermingled, and the like.

Spectral Labeling

Figure 1:
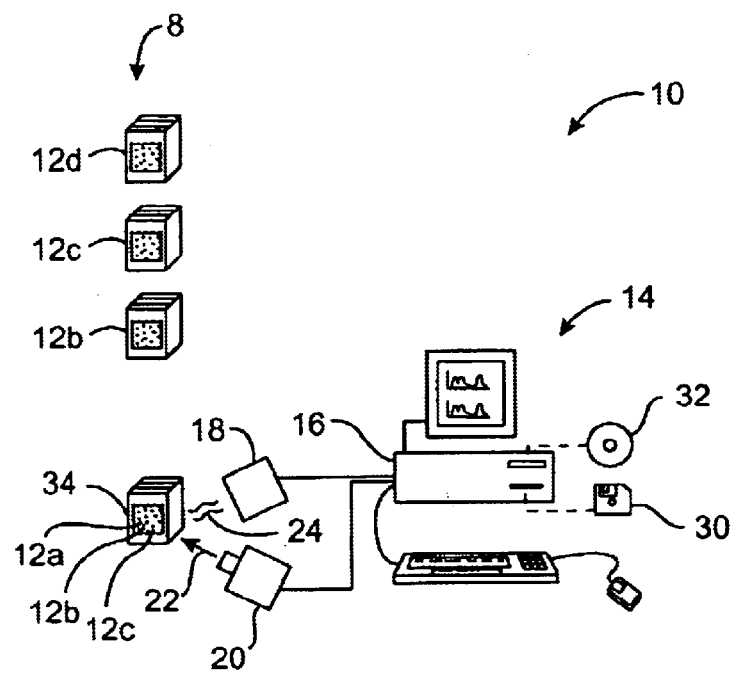
FIG. 1 schematically illustrates an imaging system and high-throughput assay method according the principles of the present invention.

Referring now to FIG. 1, an inventory system 10 includes a library of labeled elements 12a, 12b, . . . (collectively referred to as elements 12) and an analyzer 14. Analyzer 14 generally includes a processor 16 coupled to a detector 18. An energy source 20 transmits an excitation energy 22 to a sensing field within a first labeled element 12a of library 8. In response to excitation energy 22, first labeled element 12a emits radiant energy 24 defining a spectral code. Spectral code of radiant energy 24 is sensed by detector 18 and the spectral code is interpreted by processor 16 so as to identify labeled element 12a.

Library 8 may optionally comprise a wide variety of elements. In many embodiments, labeled elements 12 may be separated. However, in the exemplary embodiment, the various labeled elements 12a, 12b, 12c, . . . are intermingled within a test fluid 34. Imaging is facilitated by maintaining the labeled elements on or near a surface. As used therein, "areal imaging" means imaging of a two-dimensional area.

Hence, fluid 34 may be contained in a thin, flat region between planar surfaces.

Preferably, detector 18 simultaneously images at least some of the signals generated by elements 12 from within a two-dimensional sensing field. In some embodiments, at least some of the spectral signals from within the sensing field are sequentially sensed using a scanning system. Regardless, maintaining each label as a spatially integral unit will often facilitate identification of the label. This discrete spatial integrity of each label is encompassed within the term "spatially resolved labels." Preferably, the spatial integrity of the beads and the space between beads will be sufficient to allow at least some of the beads to be individually resolved over all other beads, preferably allowing most of the beads to be individually resolved, and in many embodiments, allowing substantially all of the beads to be individually resolved.

The spectral coding of the present invention is particularly well-suited for identification of small or fluid elements which may be difficult to label using known techniques. Elements 12 may generally comprise a composition of matter, a biological structure, a fluid, a particle, an article of manufacture, a consumer product, a component for an assembly, or the like. All of these are encompassed within the term "identifiable substance."

The labels included with labeled elements 12 may be adhered to, applied to a surface of, and/or incorporated within the items of interest, optionally using techniques analogous to those of standard bar coding technologies. For example, spectral labeling compositions of matter (which emit the desired spectra) may be deposited on adhesive labels and applied to articles of manufacture. Alternatively, an adhesive polymer material incorporating the label might be applied to a surface of a small article, such as a jewel or a component of an electronic assembly. As the information in the spectral code does not depend upon the aerial surface of the label, such labels can be quite small.

In other embodiments, the library will comprise fluids (such as biological samples), powders, cells, and the like. While labeling of such samples using standard bar coding techniques can be quite problematic, particularly when a large number of samples are to be accurately identified, the spectral codes of the present invention can allow robust identification of a particular element from among ten or more library elements, a hundred or more library elements, a thousand or more library elements, and even ten thousand or more library elements.

The labels of the labeled elements 12 will often include compositions of matter which emit energy with a controllable wavelength/intensity spectrum. To facilitate identification of specific elements from among library 8, the labels of the elements may include combinations of differing compositions of matter to emit differing portions of the overall spectral code. In other embodiments, the signals may be defined by absorption (rather than emission) of energy, by Raman scattering, or the like. As used herein, the term "markers" encompasses compositions of matter which produce the different signals making up the overall spectra. A plurality of markers can be combined to form a label, with the signals from the markers together defining the spectra for the label.

The present invention generally utilizes a spectral code comprising one or more signals from one or more markers. The markers may comprise semiconductor nanocrystals, with the different markers often taking the form of different particle size distributions of semiconductor nanocrystals having different signal generation characteristics. The combined markers define labels which can generate spectral codes, which are sometimes referred to as "spectral barcodes." These spectral codes can be used to track the location of a particular item of interest or to identify a particular item of interest. The semiconductor nanocrystals used in the spectral coding scheme can be tuned to a desired wavelength to produce a characteristic spectral emission or signal by changing the composition and/or size of the semiconductor nanocrystal. Additionally, the intensity of the signal at a particular characteristic wavelength can also be varied (optionally by, at least in part, varying a number of semiconductor nanocrystals emitting or absorbing at a particular wavelength), thus enabling the use of binary or higher order encoding schemes. The information encoded by the semiconductor nanocrystals can be spectroscopically decoded from the characteristics of their signals, thus providing the location and/or identity of the particular item or component of interest. As used herein, wavelength and intensity are encompassed within the term "signal characteristics."

While spectral codes will often be described herein with reference to the signal characteristics of signals emitted with discrete, narrow peaks, it should be understood that semiconductor nanocrystals and other marker structures may generate signals having quite different properties. For example, signals may be generated by scattering, absorption, or the like, and alternative signal characteristics such as wavelength range width, slope, shift, or the like may be used in some spectral coding schemes.

Semiconductor Nanocrystals

Semiconductor nanocrystals are particularly well-suited for use as markers in a spectral code system because of their unique characteristics. Semiconductor nanocrystals have radii that are smaller than the bulk exciton Bohr radius and constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of semiconductor nanocrystals shift to the blue (higher energies) with decreasing size. Upon exposure to a primary light source, each semiconductor nanocrystal distribution is capable of emitting energy in narrow spectral linewidths, as narrow as 20–30 nm, and with a symmetric, nearly Gaussian line shape, thus providing an easy way to identify a particular semiconductor nanocrystal. The linewidths are dependent on the size heterogeneity, i.e., monodispersity, of the semiconductor nanocrystals in each preparation. Single semiconductor nanocrystal complexes have been observed to have full width at half max (FWHM) as narrow as 12–15 nm. In addition semiconductor nanocrystal distributions with larger linewidths in the range of 40–60 nm can be readily made and have the same physical characteristics as semiconductor nanocrystals with narrower linewidths.

Exemplary materials for use as semiconductor nanocrystals in the present invention include, but are not limited to group II–VI, III–V, and group IV semiconductors such as ZnS, ZnSe, ZnTe, CdS, CdSe, CdTe, GaN, GaP, GaAs, GaSb, InP, InAs, InSb, AlS, AlP, AlSb, PbS, PbSe, Ge, Si, and ternary and quaternary mixtures or alloys thereof. The semiconductor nanocrystals are characterized by their nanometer size. By "nanometer" size, it is meant less than about 150 Angstroms (A), and preferably in the range of 12–150 A.

The selection of the composition of the semiconductor nanocrystal, as well as the size of the semiconductor nanocrystal, affects the signal characteristics of the semiconductor nanocrystal. Thus, a particular composition of a semiconductor nanocrystal as listed above will be selected based upon the spectral region being monitored. For example, semiconductor nanocrystals that emit energy in the visible range include, but are not limited to, CdS, CdSe, CdTe, and ZnTe. Semiconductor nanocrystals that emit energy in the near IR range include, but are not limited to, InP, InAs, InSb, PbS, and PbSe. Finally, semiconductor nanocrystals that emit energy in the blue to near-ultraviolet include, but are not limited to, ZnS and GaN. For any particular composition selected for the semiconductor nanocrystals to be used in the inventive system, it is possible to tune the emission to a desired wavelength within a particular spectral range by controlling the size of the particular composition of the semiconductor nanocrystal.

In addition to the ability to tune the signal characteristics by controlling the size of a particular semiconductor nanocrystal, the intensities of that particular emission observed at a specific wavelength are also capable of being varied, thus increasing the potential information density provided by the semiconductor nanocrystal coding system. In some embodiments, 2–15 different intensities may be achieved for a particular emission at a desired wavelength, however, more than fifteen different intensities may be achieved, depending upon the particular application of the inventive identification units. For the purposes of the present invention, different intensities may be achieved by varying the concentrations of the particular size semiconductor nanocrystal attached to, embedded within or associated with an item or component of interest, by varying a Quantum yield of the nanocrystals, by varyingly quenching the signals from the semiconductor nanocrystals, or the like. Nonetheless, the spectral coding schemes may actually benefit from a simple binary structure, in which a given wavelength is either present our absent, as described below.

In a particularly preferred embodiment, the surface of the semiconductor nanocrystal is also modified to enhance the efficiency of the emissions, by adding an overcoating layer to the semiconductor nanocrystal. The overcoating layer is particularly preferred because at the surface of the semiconductor nanocrystal, surface defects can result in traps for electron or holes that degrade the electrical and optical properties of the semiconductor nanocrystal. An insulting layer (having a bandpass layer typically with a bandgap energy greater than the core and centered thereover) at the surface of the semiconductor nanocrystal provides an atomically abrupt jump in the chemical potential at the interface that eliminates energy states that can serve as traps for the electrons and holes. This results in higher efficiency in the luminescent process.

Suitable materials for the overcoating layer include semiconductors having a higher band gap energy than the semiconductor nanocrystal. In addition to having a band gap energy greater than the semiconductor nanocrystals, suitable materials for the overcoating layer should have good conduction and valence band offset with respect to the semiconductor nanocrystal. Thus, the conduction band is desirably higher and the valence band is desirably lower than those of the semiconductor nanocrystal. For semiconductor nanocrystals that emit energy in the visible (e.g., CdS, CdSe, CdTe, ZnSe, ZnTe, GaP, GaAs) or near IR (e.g., InP, InAs, InSb, PbS, PbSe), a material that has a band gap energy in the ultraviolet regions may be used. Exemplary materials include ZnS, GaN, and magnesium chalcogenides, (e.g., MgS, MgSe, and MgTe). For semiconductor nanocrystals that emit in the near IR, materials having a band gap energy in the visible, such as CdS, or CdSe, may also be used. While the overcoating will often have a higher bandgap than the emission energy, the energies can be, for example, both within the visible range. The overcoating layer may include as many as 8 monolayers of the semiconductor material. The preparation of a coated semiconductor nanocrystal may be found in U.S. patent application Ser. No. 08/969,302 filed Nov. 13, 1997, entitled "Highly Luminescent Color-Selective Materials"; Dabbousi et al., *J. Phys. Chem B.*, Vol. 101, 1997, pp. 9463; and Kuno et al., *J. Phys. Chem.*, Vol. 106, 1997, pp. 9869. Fabrication and combination of the differing populations of semiconductor nanocrystals may be further understood with reference to U.S. patent application Ser. No. 09/397,432, previously incorporated herein by reference.

It is often advantageous to combine different markers of a label into one or more labeled body. Such labeled bodies may help spatially resolve different labels from intermingled items of interest, which can be beneficial during identification. These label bodies may comprise a composition of matter including a polymeric matrix and a plurality of semiconductor nanocrystals, which can be used to encode discrete and different absorption and emission spectra. These spectra can be read using a light source to cause the label bodies to absorb or emit light. By detecting the light absorbed and/or emitted, a unique spectral code may be identified for the labels. In some embodiments, the labeled bodies may further include markers beyond the label bodies. These labeled bodies will often be referred to as "beads" herein, and beads which have assay capabilities may be called "probes." The structure and use of such probes, including their assay capabilities, are more fully described in U.S. patent application Ser. No. 09/566,014, previously incorporated herein by reference.

Figure 1A:
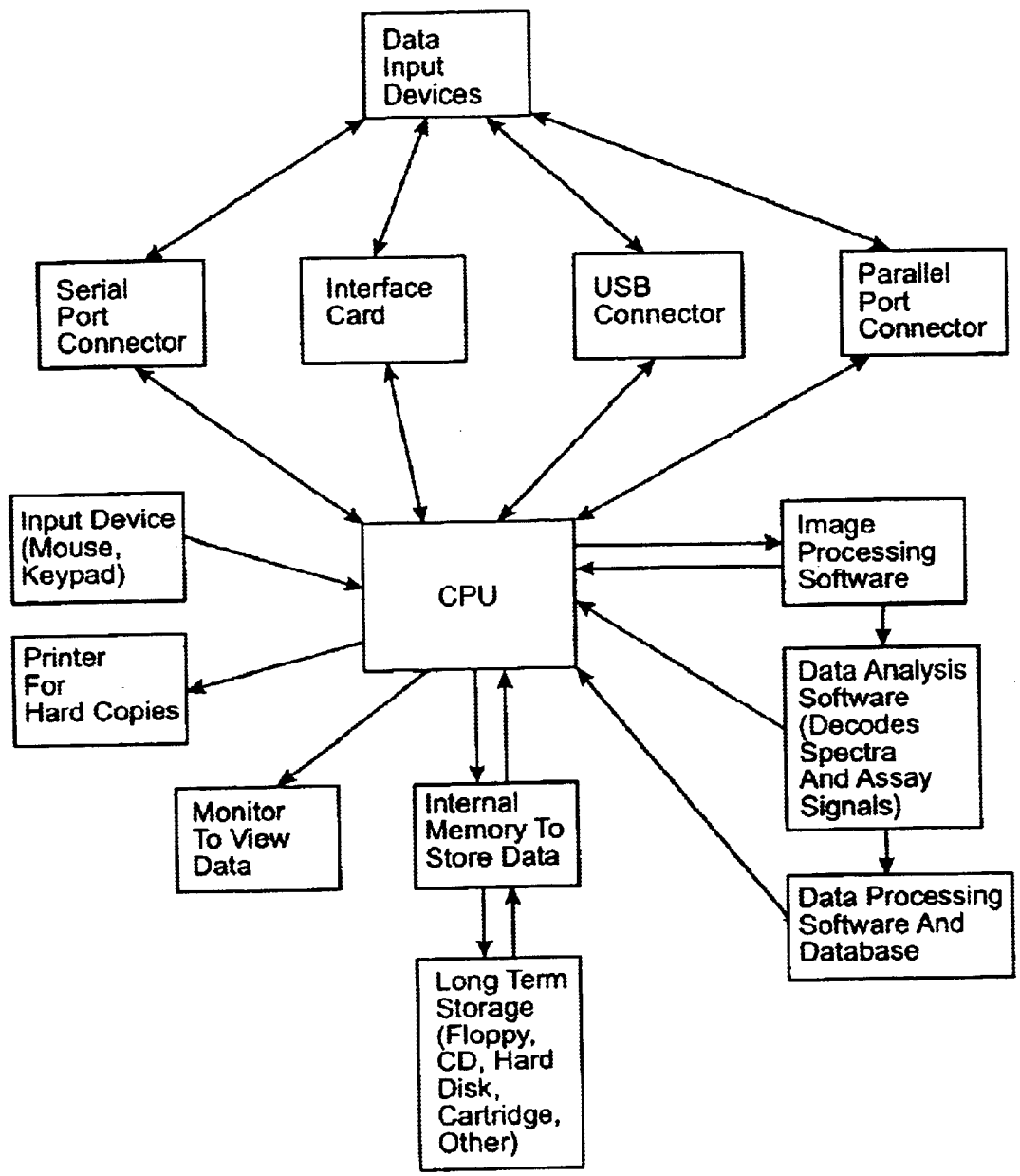
FIG. 1A schematically illustrates an exemplary processor for the system of claim 1.
Figure 2A:
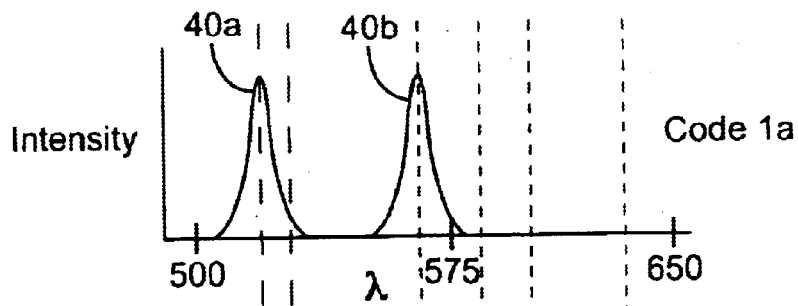
FIGS. 2A–2E schematically illustrate spectral codes or labels having a plurality of signals.
Figure 2B:
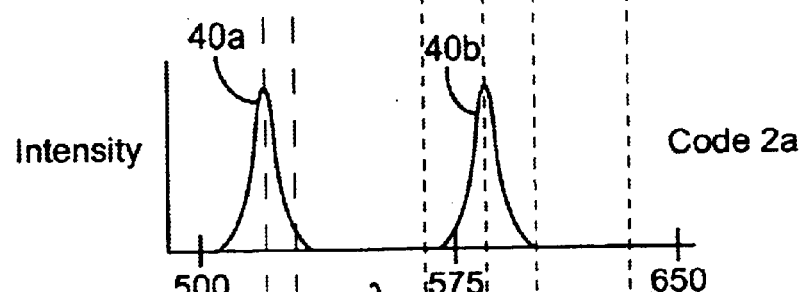
Figure 2C:
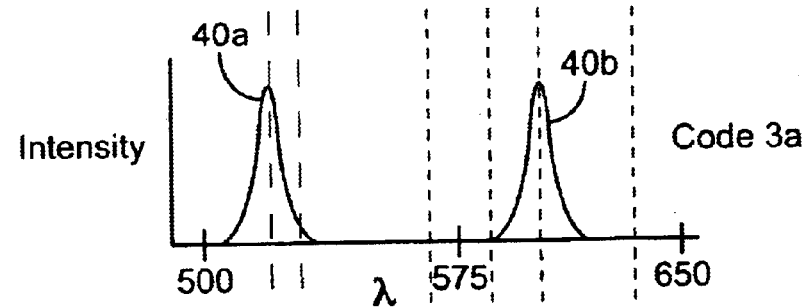
Figure 2D:
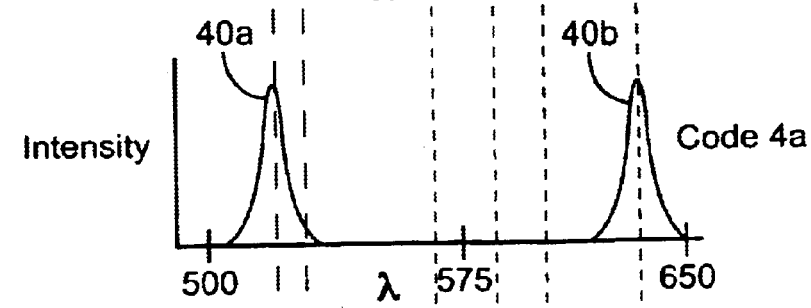
Figure 2E:
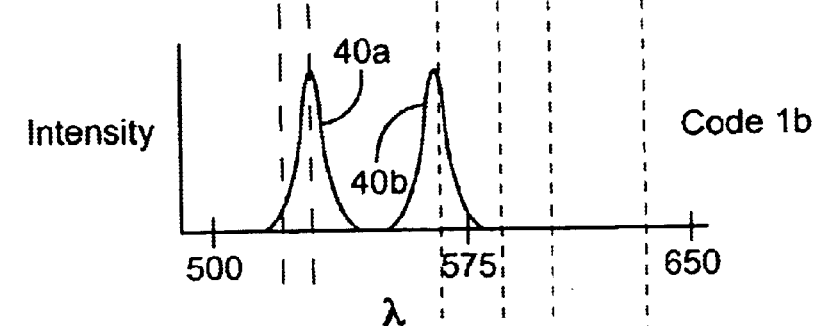

An exemplary processor is illustrated in FIG. 1A. A processor includes data input devices, a serial port connector, an interface card, a USB Connector, a parallel port connector, an input device, a printer for hard copies, a CPU, a monitor to view data, an internal memory to store data, long term storage (Floppy, CD, Hard Disk, Cartridge, Other), image processing software, data analysis software (decodes spectra and assay signals), data processing software and database.

Fabrication of Labeled Beads

Figure 2:
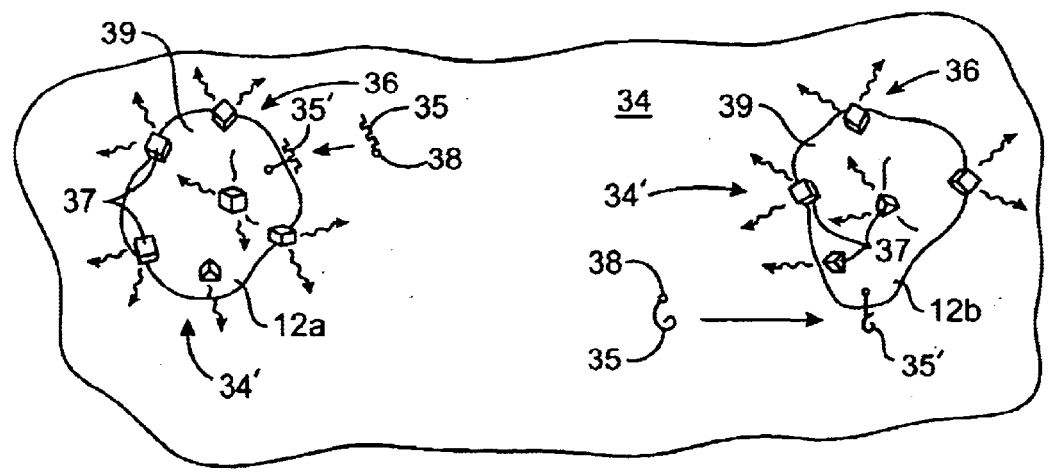
FIG. 2 schematically illustrates probes having spectral labels and assay markers, in which the probes comprise bead structures disposed within a test fluid.

Referring now to FIG. 2, first and second labeled elements 12a, 12b within test fluid 34 are formed as separate semiconductor nanocrystal probes 34'. Each probe includes an associated label 36 formed from one or more populations of substantially mono-disperse semiconductor nanocrystals 37. The individual populations of semiconductor nanocrystals will often be mono-disperse so as to provide a sufficient signal intensity at a uniform wavelength for convenient sensing of the various signals within the code. The exemplary probes further include one or more binding moieties 35', together with a probe matrix or body material 39, which acts as a binding agent to keep the various markers together in a structural unit or bead. Binding moieties 35' help (indirectly) to generate signals indicating results of an assay, each probe moiety having selective affinity for an associated test substance 35 which may be present within sample fluid 34. Probe moieties 35' may comprise an antibody, DNA, or the like, and test substances 35 may carry reporters or assay markers 38 for generating signals indicating results of the assays. Alternatively, the assay markers may have selective affinity for the combination of a particular test substance and bound probe moiety, or the like. Preparation of the spectrally encoded probes will now be described, followed by a brief description of the use and structure of assay markers 38.

A process for encoding spectra into label body materials using a feedback system can be based on the absorbance and luminescence of the semiconductor nanocrystals in a solution that can be used to dye the materials. More specifically, this solution can be used for encoding of a plurality of semiconductor nanocrystals into a material when that material is a polymeric bead.

A variety of different materials can be used to prepare these compositions. In particular, polymeric bead materials are an appropriate format for efficient multiplexing and demultiplexing of finite-sized materials. These label body beads can be prepared from a variety of different polymers, including but not limited to polystyrene, cross-linked polystyrene, polyacrylic, polysiloxanes, polymeric silica, latexes, dextran polymers, epoxies, and the like. The materials have a variety of different properties with regard to swelling and porosity, which are well understood in the art. Preferably, the beads are in the size range of approximately 10 nm to 1 mm, more preferably in a size range of approximately 100 nm to 0.1 mm, often being in a range from 1000 nm to 10,000 nm, and can be manipulated using normal solution techniques when suspended in a solution.

Discrete emission spectra can be encoded into these materials by varying the amounts and ratios of different semiconductor nanocrystals, either the size distribution of semiconductor nanocrystals, the composition of the semiconductor nanocrystals, or other property of the semiconductor nanocrystals that yields a distinguishable emission spectrum, which are embedded into, attached to or otherwise associated with the material. The semiconductor nanocrystals of the invention can be associated with the material by adsorption, absorption, covalent attachment, by co-polymerization or the like. The semiconductor nanocrystals have absorption and emission spectra that depend on their size and composition. These semiconductor nanocrystals can be prepared as described in Murray et. al., (1993) *J. Am. Chem. Soc.* 115:8706–8715; Guzelian et. al., (1996) *J. Phys. Chem.* 100;7212–7219; or International Publication No. WO 99/26299 (inventors Bawendi et al.). The semiconductor nanocrystals can be made further luminescent through overcoating procedures as described in Danek et. al., (1966) *Chem. Mat.* 8(1):173–180; Hines et. al., (1996) *J. Phys. Chem.* 100:468–471; Peng et. al., (1997) *J. Am. Chem. Soc.* 119:7019–7029; or Daboussi et. al., (1997) *J. Phys. Chem.-B.* 101:9463–9475.

The desired spectral emission properties may be obtained by mixing semiconductor nanocrystals of different sizes and/or compositions in a fixed amount and ratio to obtain the desired spectrum. The spectral emission of this staining solution can be determined prior to treatment of the material therewith. Subsequent treatment of the material (through covalent attachment, co-polymerization, passive absorption, swelling and contraction, or the like) with the staining solution results in a material having the designed spectral emission property. These spectra may be different under different excitation sources. Accordingly, it is preferred that the light source used for the encoding procedure be as similar as possible (preferably of the same wavelength and/or intensity) to the light source that will be used for the decoding. The light source may be related in a quantitative manner, so that the emission spectrum of the final material may be deduced from the spectrum of the staining solution.

A number of semiconductor nanocrystal solutions can be prepared, each having a distinct distribution of sizes and compositions, and consequently a distinct emission spectrum, to achieve a desired emission spectrum. These solutions may be mixed in fixed proportions to arrive at a spectrum having the predetermined ratios and intensities of emission from the distinct semiconductor nanocrystals suspended in that solution. Upon exposure of this solution to a light source, the emission spectrum can be measured by techniques that are well established in the art. If the spectrum is not the desired spectrum, then more of a selected semiconductor nanocrystal solution can be added to achieve the desired spectrum and the solution titrated to have the correct emission spectrum. These solutions may be colloidal solutions of semiconductor nanocrystals dispersed in a solvent, or they may be pre-polymeric colloidal solutions, which can be polymerized to form a matrix with semiconductor nanocrystals contained within. While ratios of the quantities of constituent solutions and the final spectrum intensities need not be the same, it will often be possible to derive the final spectra from the quantities (and/or the quantities from the desired spectra.)

The solution luminescence will often be adjusted to have the desired intensities and ratios under the exact excitation source that will be used for the decoding. The spectrum may also be prepared to have an intensity and ratio among the various wavelengths that are known to produce materials having the desired spectrum under a particular excitation source. A multichannel auto-pipettor connected to a feedback circuit can be used to prepare a semiconductor nanocrystal solution having the desired spectral characteristics, as described above. If the several channels of the titrator/pipettor are charged or loaded with several unique solutions of semiconductor nanocrystals, each having a unique excitation and emission spectrum, then these can be combined stepwise through addition of the stock solutions. In between additions, the spectrum may be obtained by exposing the solution to a light source capable of causing the semiconductor nanocrystals to emit, preferably the same light source that will be used to decode the spectra of the encoded materials. The spectrum obtained from such intermediate measurements may be judged by a computer based on the desired spectrum. If the solution luminescence is lacking in one particular semiconductor nanocrystal emission spectrum, stock solution containing that semiconductor nanocrystal may be added in sufficient amount to bring the emission spectrum to the desired level. This procedure can be carried out for all different semiconductor nanocrystals simultaneously, or it may be carried out sequentially.

Once the staining solution has been prepared, it can be used to incorporate a unique luminescence spectrum into the materials of this invention. If the method of incorporation of the semiconductor nanocrystals into the materials is absorption or adsorption, then the solvent that is used for the staining solution may be one that is suitable for swelling the materials. Such solvents are commonly from the group of solvents including dichloromethane, chloroform, dimethylformamide, tetrahydrofuran and the like. These can be mixed with a more polar solvent, for example methanol or ethanol, to control the degree and rate of incorporation of the staining solution into the material. When the material is added to the staining solution, the material will swell, thereby causing the material to incorporate a plurality of semiconductor nanocrystals in the relative proportions that are present in the staining solution. In some embodiments, the semiconductor nanocrystals may be incorporated in a different but predictable proportion. When a more polar solvent is added, after removal of the staining solution from the material, material shrinks, or unswells, thereby trapping the semiconductor nanocrystals in the material. Alternatively, semiconductor nanocrystals can be trapped by evaporation of the swelling solvent from the material. After rinsing with a solvent in which the semiconductor nanocrystals are soluble, yet that does not swell the material, the semiconductor nanocrystals are trapped in the material, and may not be rinsed out through the use of a non-swelling, non-polar solvent. Such a non-swelling, non-polar solvent is typically hexane or toluene. The materials can be separated and then exposed to a variety of solvents without a change in the emission spectrum under the light source. When the material used is a polymer bead, the material can be separated from the rinsing solvent by centrifugation or evaporation or both, and can be redispersed into aqueous solvents and buffers through the use of detergents in the suspending buffer, as is well known in the art.

The above procedure can be carried out in sequential steps as well. A first staining solution can be used to stain the materials with one population of semiconductor nanocrystals. A second population of semiconductor nanocrystals can be prepared in a second staining solution, and the material exposed to this second staining solution to associate the semiconductor nanocrystals of the second population with the material. These steps can be repeated until the desired spectral properties are obtained from the material when excited by a light source, optionally using feedback from measurements of the interim spectra generated by the partially stained bead material to adjust the process.

The semiconductor nanocrystals can be attached to the material by covalent attachment, and/or by entrapment in pores of the swelled beads. For instance, semiconductor nanocrystals are prepared by a number of techniques that result in reactive groups on the surface of the semiconductor nanocrystal. See, e.g., Bruchez et. al., (1998) *Science* 281:2013–2016; and Ghan et. al., (1998) *Science* 281:2016–2018, Golvin et. al., (1992) *J. Am. Chem. Soc.* 114:5221–5230; Katari et. al. (1994) *J. Phys. Chem.* 98:4109–4117; Steigerwald et. al. (1987) *J. Am. Chem. Soc.* 110:3046. The reactive groups present on the surface of the semiconductor nanocrystals can be coupled to reactive groups present on the surface of the material. For instance, semiconductor nanocrystals which have carboxylate groups present on their surface can be coupled to beads with amine groups using a carbo-diimide activation step, or a variety of other methods well known in the art of attaching molecules and biological substances to bead surfaces. In this case, the relative amounts of the different semiconductor nanocrystals can be used to control the relative intensities, while the absolute intensities can be controlled by adjusting the reaction time to control the number of reacted sites in total. After the bead materials are stained with the semiconductor nanocrystals, the materials are optionally rinsed to wash away unreacted semiconductor nanocrystals.

Referring once again to FIG. 2, labeled elements 12a, 12b (here in the form of semiconductor nanocrystal probes) may be useful in assays in a wide variety of forms. Utility of the probes for assays benefits significantly from the use of moieties or affinity molecules 35', as schematically illustrated in FIG. 2, which may optionally be supported directly by a label marker 37 of label 36, by the probe body matrix 39, or the like. Moieties 35' can have selective affinity for an associated detectable substance 35, as schematically illustrated by correspondence symbol shapes in FIG. 2. The probes may, in some embodiments, also include an integrated assay marker 38 which is activated or enabled to generate a signal by the binding of probe moiety 35' to test substance 35. In many embodiments, the assay marker will instead be coupled to the probes by coupling of detectable substance 35 to moiety 35'. In other words, the assay marker 38 may (at least initially) be coupled to the detectable substance 35, typically by binding of a dye molecule, incorporation of a radioactive isotope, or the like. The assay markers may thus be coupled to the probe by the interaction between the moieties 35' and the test or detectable substances 35. In other assays, the assay results may be determined by the presence or absence of the probe or bead (for example, by washing away probes having an unattached moiety) so that no dedicated assay marker need be provided.

In alternative embodiments, the material used to make the codes does not need to be semiconductor nanocrystals. For example, any fluorescent material or combination of fluorescent materials that can be finely tuned throughout a spectral range and can be excited optically or by other means might be used. For organic dyes, this may be possible using a number of different dyes that are each spectrally distinct.

This bead preparation method can be used generically to identify identifiable substances, including cells and other biological matter, objects, and the like. Pre-made mixtures of semiconductor nanocrystals, as described above, are attached to objects to render them subsequently identifiable. Many identical or similar objects can be coded simultaneously, for example, by attaching the same semiconductor nanocrystal mixture to a batch of microspheres using a variety of chemistries known in the art. Alternatively, codes may be attached to objects individually, depending on the objects being coded. In this case, the codes do not have to be pre-mixed and may be mixed during application of the code, for example using an inkjet printing system to deliver each species of semiconductor nanocrystals to the object. The use of semiconductor nanocrystal probes in chemical and/or biological assays is more fully described in U.S. patent application Ser. No. 09/566,014, the full disclosure of which is incorporated herein by reference.

The semiconductor nanocrystal probes of FIG. 2 may also be utilized to detect the occurrence of an event. This event, for example, may cause the source from which energy is transferred to assay marker 38 to be located spatially proximal to the semiconductor nanocrystal probe. Hence, the excitation energy from energy source 20 may be transferred either directly to assay markers 38, 38', or indirectly via excitation of one or more energy sources adjacent the semiconductor nanocrystal probes due to bonding of the test substances 35 to the moiety 35'. For example, a laser beam may be used to excite a proximal source such as a semiconductor nanocrystal probe 38' attached to one of the test substances 35 (to which the affinity molecule selectively attaches), and the energy emitted by this semiconductor nanocrystal 38' may then excite an assay marker 38 affixed to the probe matrix. As mentioned above, still further assay marker structures and methods are described in detail in co-pending U.S. patent application Ser. No. 09/566,014.

Reading Beads

Referring once again to FIG. 1, energy source 20 generally directs excitation energy 22 in such a form as to induce emission of the spectral code from labeled element 12a. In one embodiment, energy source 20 comprises a source of light, the light preferably having a wavelength shorter than that of the spectral code. Energy source 20 may comprise a source of blue or ultraviolet light, optionally comprising a broad band ultraviolet light source such a deuterium lamp, optionally with a filter. Alternatively, energy source 20 may comprise an Xe or Hg UV lamp, or a white light source such as a xenon lamp or a deuterium lamp, preferably with a short pass or bandpass filter disposed along the excitation energy path from the lamp to the labeled elements 12 so as to limit the excitation energy to the desired wavelengths. Still further alternative excitation energy sources include any of a number of continuous wave (cw) gas lasers, including (but not limited to) any of the argon ion laser lines (457 nm, 488 nm, 514 nm, etc.), a HeCd laser, a solid-state diode laser (preferably having a blue or ultraviolet output such as a GaN based laser, a GaAs based laser with frequency doubling, a frequency doubled or tripled output of a YAG or YLF based laser, or the like), any of the pulsed lasers with an output in the blue or ultraviolet ranges, light emitting diodes, or the like, or any other laser source (solid, liquid, or gas based) with emissions to the blue of the code spectrum.

The excitation energy 22 from energy source 20 will induce labeled element 12a to emit identifiable energy 24 having the spectral code, with the spectral code preferably comprising signals having relatively narrow peaks so as to define a series of distinguishable peak wavelengths and associated intensities. The peaks will typically have a half width of about 100 nm or less, preferably of 70 nm or less, more preferably 50 nm or less, and ideally 30 nm or less. In many embodiments, a plurality of separate signals will be included in the spectral code as sensed by sensor 18. As semiconductor nanocrystals are particularly well-suited for generating luminescent signals, identifiable energy 24 from label 12a will often comprise light energy. To help interpret the spectral code from the identifiable energy 24, the light energy may pass through one or more monochromator or other wavelength dispersive element. A Charge-Coupled Device (CCD) camera or some other two-dimensional detector of sensor 18 can sense and/or record the images for later analysis. In other embodiments, a scanning system maybe employed, in which the labeled element to be identified is scanned with respect to a microscope objective, with the luminescence put through a single monochromator or a grating or prism to spectrally resolve the colors. The detector can be a diode array that records the colors that are emitted at a particular spatial position, a two-dimensional CCD, or the like.

Information regarding these spectra from the labeled elements 12 will generally be transmitted from sensor 18 to processor 16, the processor typically comprising a general purpose computer. Processor 16 will typically include a central processing unit, ideally having a processing capability at least equivalent to a Pentium I® processor, although simpler systems might use processing capabilities of a Palm® handheld processor or more. Processor 16 will generally have input and output capabilities and associated peripheral components, including an output device such as a monitor, an input such as a keyboard, mouse, and/or the like, and will often have a networking connection such as an Ethernet, an Intranet, an Internet, and/or the like. An exemplary processing block diagram is schematically illustrated in FIG. 1A.

Processor 16 will often make use of a tangible media 30 having a machine-readable code embodying method steps according to one or more methods of the present invention. A database 32, similarly embodied on a machine-readable code, will often include a listing of the elements included in library 8, the spectral codes of the labels associated with the elements, and a correlation between specific library elements and their associated codes. Processor 16 uses the information from database 32 together with the spectrum characteristics sensed by sensor 18 to identify a particular library element 12a. The machine-readable code of program instructions 30 and database 32 may take a wide variety of forms, including floppy disks, optical discs (such as CDs, DVDs, rewritable CDs, and the like), alternative magnetic recording media (such as tapes, hard drives, and the like), volatile and/or non-volatile memories, software, hardware, firmware, or the like.

As illustrated in FIG. 1, methods for detecting and classifying spectral labels (such as encoded materials and beads) may comprise exposing the labels to light of an excitation source so that the semiconductor nanocrystals of the label are sufficiently excited to emit light. This excitation source is preferably of an energy capable of exciting the semiconductor nanocrystals to emit light and may be of higher energy (and hence, shorter wavelength) than the shortest emission wavelength of the semiconductor nanocrystals in the label. Alternatively the excitation source can emit light of longer wavelength if it is capable of exciting some of the semiconductor nanocrystals disposed in the matrix to emit light, such as using two-photon excitation. This excitation source is preferably chosen to excite a sufficient number of different populations of semiconductor nanocrystals to allow unique identification of the encoded materials. For example, using materials stained in a 1:2 ratio of red to blue and a 1:3 ratio of red to blue, it may not be sufficient to only excite the red emitting semiconductor nanocrystals (e.g., by using green or yellow light) of the sample in order to resolve these beads. It would be desirable to use a light source with components that are capable of exciting the blue emitting and the red emitting semiconductor nanocrystals simultaneously, (e.g., violet or ultraviolet). There may be one or more light sources used to excite the populations of the different semiconductor nanocrystals simultaneously or sequentially, but each light source may selectively excite sub-populations of semiconductor nanocrystals that emit at lower energy than the light source (to a greater degree than higher energy emitting sub-populations), due to the absorbance spectra of the semiconductor nanocrystals. Ideally, a single excitation energy source will be sufficient to induce the labels to emit identifiable spectra.

Spectral Codes

Referring now to FIGS. 2A–2E, the use of a plurality of different signals within a single spectral label can be understood. In this simple example, a coding system is shown having two signals. A first signal has a wavelength peak 40a at a first discreet wavelength, while a separate signal has a different wavelength peak 40b. As shown in FIGS. 2A–2D, varying peak 40b while the first peak 40a remains at a fixed location defines a first family of spectral codes la through 4a. Moving the first peak 40a to a new location allows a second family of spectral codes to be produced, as can be understood with reference to FIG. 2E.

The simple code system illustrated in FIGS. 2A–2E includes only two signals, but still allows a large number of identifiable spectra. More complex spectral codes having larger numbers of peaks can significantly increase the number of codes. Additionally, the intensities of one or more of the peaks may also be varied, thereby providing still higher order codes having larger numbers of separately identifiable members.

Spectral Code Reading Systems

In general, fluorescent labeling is a powerful technique for tracking components in biological systems. For instance, labeling a portion of a cell with a fluorescent marker can allow one to monitor the movement of that component within the cell. Similarly, labeling an analyte in a bioassay can allow one to determine its presence or absence, even at vanishingly small concentrations. The use of multiple fluorophores with different emission wavelengths allows different components to be monitored simultaneously. Applications such as spectral encoding can take full advantage of multicolor fluorophores, potentially allowing the simultaneous detection of millions of analytes.

When imaging samples labeled with multiple chromophores, it is desirable to resolve spectrally the fluorescence from each discrete region within the sample. As an example, an assay may be prepared in which polymer beads have been labeled with two different chromophores and the results of the assay may be determined by the ratio of the two types of beads within the final sample. One could imagine immobilizing the beads and counting each of the colors. Electronic imaging requires a technique for acquiring an image of the sample in which spectral information is available at each discrete point. While the human eye is exceptionally good at distinguishing colors, typical electronic photodetectors are often effectively color-blind. As such, additional optical components are often used in order to acquire spectral information.

Many techniques might be applied to solve this problem. Fourier transform spectral imaging (Malik et al. (1996) *J. Microsc.* 182:133; Brenan et al. (1994) *Appl. Opt* 33:7520) and Hadamard transform spectral imaging (Treado et al. (1989) *Anal. Chem* 61:732A; Treado et al. (1990) *Appl. Spectrosc.* 44:1–4; Treado et al. (1990) *Appl. Spectrosc.* 44:1270; Hammaker et al. (1995) *J. Mol. Struct.* 348:135; Mei et al. (1996) *J. Anal. Chem.* 354:250; Flateley et al. (1993) *Appl. Spectrosc.* 47:1464), imaging through variable interference (Youvan (1994) *Nature* 369:79; Goldman et al. (1992) *Biotechnology* 10:1557), acousto-optical (Mortensen et al. (1996) *IEEE Trans. Inst. Meas.* 45:394; Turner et al (1996) *Appl. Spectrosc.* 50:277) or liquid crystal filters (Morris et al. (1994) *Appl. Spectrosc.* 48:857) or simply scanning a slit or point across the sample surface (Colarusso et al. (1998) *Appl. Spectrosc.* 52:106A) are methods capable of generating spectral and spatial information across a two-dimensional region of a sample. Most of these techniques, however, benefit from the mechanical scanning of one component of the system as well as the acquisition of multiple data frames in order to generate a spectral image. For instance, Fourier transform imaging scans an interferometer, acquiring a full image at each mirror position. The spectral information is then extracted from the complete set of spatial images. Similarly, "point scanning" typically relies on a full spectrum from each position within the image and scans all positions to generate the full image. These techniques may allow precise spectral fitting and analysis, but may be too cumbersome and slow for highly multiplexed systems.

Figure 3:
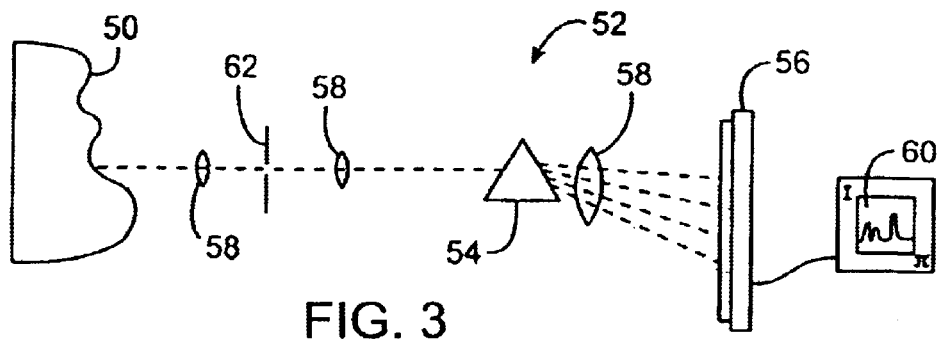
FIG. 3 schematically illustrates a system and method for determining a spectrum from a relatively large object by use of an aperture.

Referring now to FIG. 3, a system and method for reading spectral information from an arbitrarily large object 50 generally makes use of a detector 52 including a wavelength dispersive element 54 and a sensor 56. Imaging optics 58 image object 50 onto a surface of sensor 56. Wavelength dispersive element 54 spectrally disperses the image across the surface of the sensor, distributing the image based on the wavelengths of the image spectra.

Figure 4:
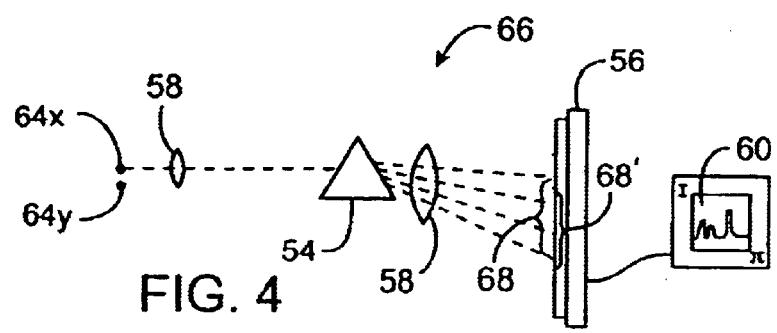
FIG. 4 schematically illustrates a method and structure for determining a spectrum from a small object, such as an assay probe having semiconductor nanocrystal markers, without using an aperture.

As object 50 is relatively large when imaged upon sensor 56, differentiation of the discreet wavelengths within a spectrum 60 is facilitated by the use of an aperture 62. As aperture 62 allows only a small region of the image through wavelength dispersive element 54, the wavelength dispersive element separates the image components based on wavelength alone (rather than on a combination of wavelength and position along the surface of image 50). Spectra 60 may then be directly determined based on the position of the diffracted image upon sensor 56, together with the intensity of image wavelength components as measured by the sensor. As the position of object 50 is scanned past aperture 62, the remainder of the spectral image can be collected. Referring now to FIG. 4, a spectra 60 of a spectrally labeled nanocrystal bead 64 may be performed using a detector 66 without an aperture. As bead 64 has a signal generating area (as imaged by imaging optics 58) which is much smaller than a sensing surface of sensor 56, bead 64 can act as a point-source of spectra 60. Optics 58 would typically, in the absence of dispersive element 54, image bead 64 on detector 56 so that the bead image has a size similar to or smaller than an aperture of a monochrometer (the undispensed image size typically being about 250 $\mu$m or less, ideally about 120 $\mu$m or less). The various signals of the spectral code emanate from small surface area of the bead, so that the signal distribution across the sensor surface is dominated by the wavelength dispersion, and no limiting of the image via an aperture is required. As used herein, a "true point source" is a light source with a dimension which is at least as small as a minimum, diffraction limited determinable dimension. A light source which is larger than a true point source may be "treated" or "analyzed" as a point source if it has a dimension or size which is sufficiently small that its size acts like an aperture.

As described above, it will often be advantageous to include a plurality of different spectrally labeled beads within a fluid. These labeled beads will often be supported by the surrounding fluid, and/or will be movable with the fluid, particularly in high-throughput multiplexed bead-based assays. Optionally, the beads may have a size sufficient to define a suspension within the surrounding test fluid. In sonic embodiments, the beads may comprise a colloid within the test fluid. In some embodiments, beads 64 may be movably supported by a surface of a vessel containing the test fluid, for example, being disposed on the bottom surface of the vessel (where beads 64 have a density greater than that of the test fluid). In other embodiments, the beads may be affixed to a support structure and/or to each other. Still further alternatives are possible, such as for beads 64 to be floating on an upper surface of the test fluid, for the bead or beads to be affixed to or disposed between cooperating surfaces of the vessel to maintain the positioning of the bead or beads, for the bead or beads to be disposed at the interface between two fluids, and the like.

Figure 5A:
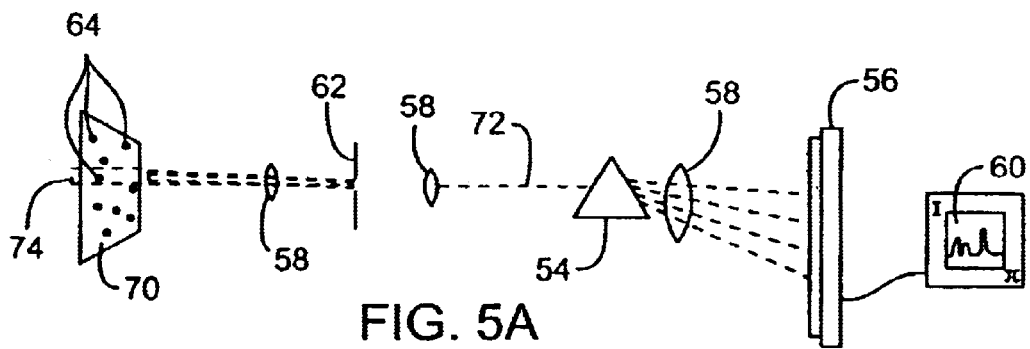
FIGS. 5A and 5B schematically illustrate a system and method for determining absolute spectra from a plurality of semiconductor nanocrystals by limiting the viewing field with an aperture and by spectrally dispersing the apertured image.

As was described above, it will often be advantageous to include numerous beads 64 within a single test fluid so as to perform a plurality of assays. Similarly, it will often be advantageous to identify a large number of fluids or small discreet elements within a single viewing area without separating out each spectral label from the combined labeled elements. As illustrated in FIG. 4, the dispersed spectral image 68 of bead 64$x$ upon sensor 56 will depend on both the relative spectra generated by the bead, and on the position of the bead. For example, bead 64$y$ is imaged onto a different portion 68' of sensor 56, which could lead to misinterpretation of the wavelengths of the spectra if the location of bead 64$y$ is not known. So long as an individual bead 64$x$ can be accurately aligned with the imaging optics 58 and sensor system 66, absolute spectral information can be obtained. However, as can be understood with reference to FIG. 5A, a plurality of beads 64 will often be distributed throughout an area 70.

Figure 5B:
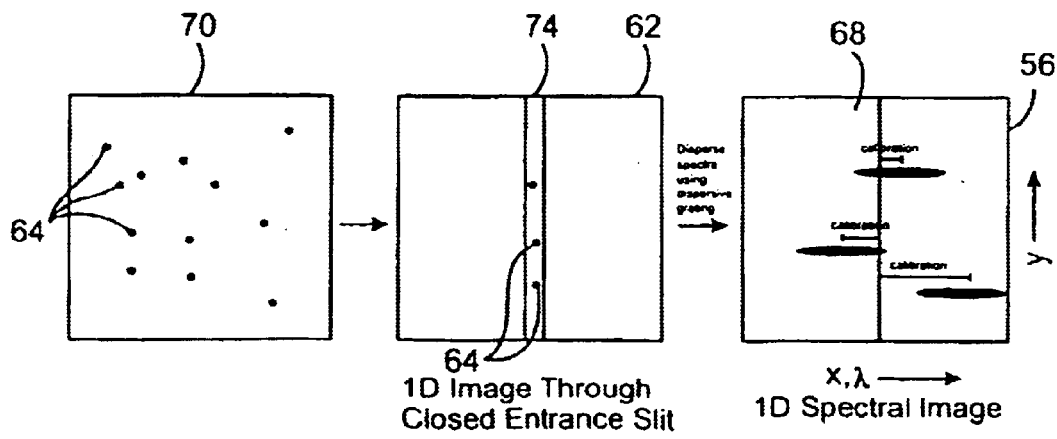

To ensure that only beads 64 which are aligned along an optical axis 72 are imaged onto sensor 56, aperture 62 restricts a sensing field 74 of the sensing system. Where sensor 56 comprises an areal sensor such a charge couple device (CCD), aperture 62 may comprise a slit aperture so that spectral wavelengths $\lambda$ can be determined from the position of the dispersed images 68 along a dispersion axis of wavelength dispersive element 54 for multiple beads 64 distributed along the slit view of sensing field 74 along a second axis y, as can be understood with reference to FIG. 5B. Absolute accuracy of the spectral readings will vary inversely with a width of aperture slit 62, and the number of readings (and hence total reading time) for reading all the beads in area 70 will be longer as the slit gets narrower. Nonetheless, the beads 64 within the two-dimensional area 70 may eventually be read by the system of FIGS. 5A and 5B with a scanning system which moves the slit relative to beads 64 (using any of a variety of scanning mechanisms, such as movable mirrors, a movable aperture, a flow of the beads passed a fixed aperture, a movement of the surface of the vessel relative to the aperture, or the like).

While the techniques described above are capable of producing spectral images, there are at least two distinct disadvantages to most scanning systems. First, most scanning systems are susceptible to mechanical or electronic failure that would not exist in a static (non-scanning) system. Second, since many data points are used to generate a single spectral image, a limit is placed on the minimum time required in order to acquire a full image. Depending on the signal levels, this time could be several minutes or more. This generally precludes the use of scanning techniques in any system in which the spatial position of each point is not fixed. For instance, imaging the two-color beads described above in an aqueous medium may be difficult with a scanning system, since the beads can diffuse to different spatial positions during the acquisition of a single spectral image.

Static spectral imaging systems, in which spectral information is acquired without scanning, are very appealing since data is acquired in a single step. An example of a static spectral imaging system is one in which a spatial image is passed though several beam-splitters, separating it into multiple images, each of which is passed though a different band-pass filter. Each resulting image provides information about a discrete region of the spectrum. The images are then projected onto a detector and the signals are recombined to produce an image that contains information about the amount of light within each band-pass. Such systems are appealing because all spectral information may be acquired simultaneously, eliminating difficulties arising from non-stationary samples. The disadvantage of a band-pass imaging system is that only a discrete number of wavelengths can be monitored, precluding detailed spectral analysis and fitting. At the same time, band-pass filters and dichroic mirrors are not 100% efficient, reducing the potential detection efficiency of multiple colors. For instance, a band-pass system using ten 10% beamsplitters and 10 bandpass filters results in a maximum of 10% detection efficiency along each channel. A system of dichroic mirrors, each with 85% transmission efficiency yields approximately 20% efficiency along the final channel.

Referring once again to FIGS. 5A and 5B, one-dimensional spectral imaging can be achieved by projecting a fluorescent image onto and/or through the entrance slit of a linear spectrometer, as shown. In this configuration, spatial information is retained along the y-axis, while spectral information (wavelengths λ) is dispersed along the x-axis, as described by Empedocles, et al. in *Phys. Rev. Lett.*, 77 (18); p. 3873 (1996). The entrance slit restricts the spatial position of the light entering the spectrometer, thereby (at least in part) defining the calibration for each spectrum. The width of the entrance slit, in part, defines the spectral resolution of the system.

Figure 6:
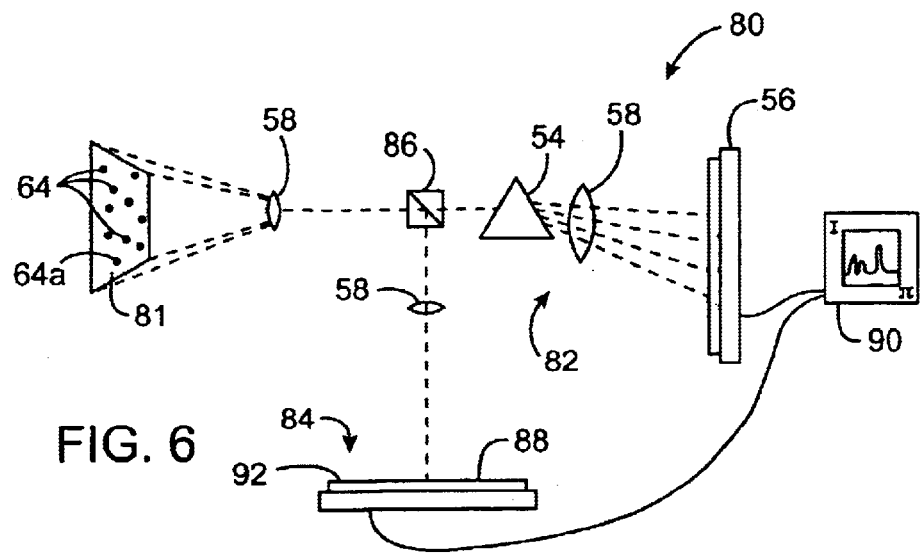
FIG. 6 schematically illustrates a system and method for determining absolute spectra of a plurality of spectrally encoded beads by simultaneously imaging the relative spectra of the beads, and by deriving the absolute spectra from the bead positions.

Referring now to FIG. 6, a two-dimensional imaging system 80 allows simultaneous sensing of spectral information from bead 64 distributed throughout a two-dimensional sensing field 81. System 80 generally makes use of a detector 82 and a system for restraining and/or identifying a position of beads 64 within two-dimensional sensing field 81. In the exemplary embodiment, the positioning system or means makes use of a bead position indicator 84. Positioning indicator 84 is optically coupled to sensing field 81. More specifically, a beam splitter 86 separates a portion of an image generated by optical train 58, and directs the image portion 88 onto a position sensor. As described above, detector 82 makes use of a wavelength dispersive element 54 and an areal sensor 56 aligned with optical train 58, hence, at least a portion of the optical path between two-dimensional sensing field 81 and the positioning system 84 is coaxial with the optical path between the sensing field 81 and sensor 56 of the detector 82.

As beads 64 are distributed across two-dimensional sensing field 81 and are not limited to a single lateral axis, wavelength dispersive element 54 will distribute the spectra from beads 64 across the surface of sensor 56 based on both the wavelength of the spectra from each bead and the associated position of the bead within the sensing field. Where beads 64 are sufficiently small in area so as to be treated as point-light sources, and where there is significantly more area surrounding the beads than the total surface area of the beads themselves so that the distributed spectra from the labels on the beads do not overlap excessively, sensor 56 can be used to determine relative spectra of the beads. For example, analyzer 90, in response to signals from sensor 56, may determine that a particular bead 64a has three equally-spaced wavelength peaks of substantially even intensity, with a fourth wavelength peak of twice the intensity of the other peaks separated from the lowest of the peaks by three times the wavelength differential between the other peaks. While such relative spectral information is useful (and may be sufficient to identify codes in some coding systems) it will often be advantageous to provide both relative and absolute spectral information for each of beads 64.

Fortunately, positioning image 88 generated upon a sensor surface 92 of position indicator 84 defines the position of beads 64 within sensing field 81. Signals transmitted from the sensor of position indicator 84 to analyzer 90 can define positions for each bead 64, and the analyzer can correlate each bead position with its associated spectra (and hence the sensed relative spectra) to determine the absolute spectrum from each bead. By taking advantage of the point-light source qualities of the relatively small beads within sensing field 81, no aperture need be included within two-dimensional system 80. In some embodiments, the positioning image and the spectrally disbursed image may be projected onto a common sensor, either sequentially or on different positions of the common sensor. Still further alternatives are possible, such as the projection of a zero-order image on the CCD for spatial information.

Stated differentially, two-dimensional images can be obtained by eliminating the entrance slit from a linear spectrometer and allowing the discrete images from individual points to define the spatial position of the light entering the spectrometer (FIG. 6). In this case, the spectral resolution of the system is defined, in part, by the size of the discrete images. Since the spatial position of the light from each point varies across the x-axis, however, the calibration for each spectrum will be different, resulting in an error in the absolute energy values. Splitting the original image and passing one half through a dispersive grating to create a separate image and spectra can eliminate this calibration error. With appropriate alignment, a correlation can be made between the spatial position and the absolute spectral energy (FIG. 6A).

Figure 6A:
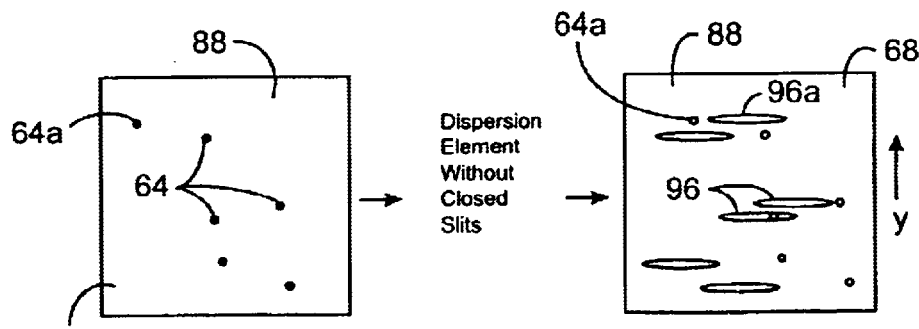
FIG. 6A schematically illustrates a method for correlating the bead positions and relative spectra sensed using the system of FIG. 6 to derive the absolute spectra.
Figure 6B:
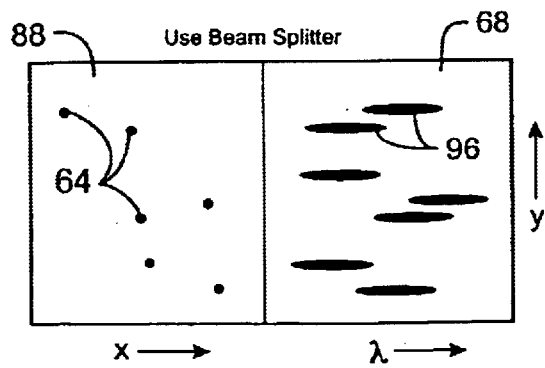
FIGS. 6B and 6C schematically illustrate the use of a beam splitter and calibration signals within the spectral codes to determine the absolute wavelengths of a spectrum.
Figure 6C:
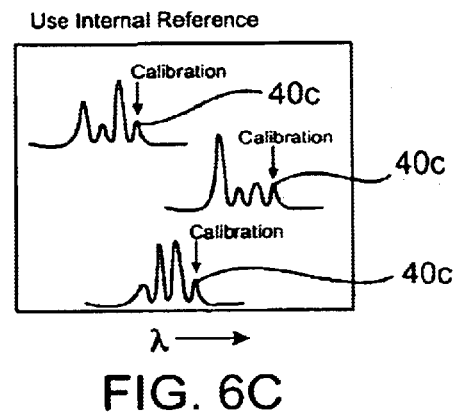

Correlation of the positioning image 88 with the spectrally dispersed image 68 can be understood with FIGS. 6A through 6C. Positioning image 88 generally indicates positions of beads 64 within sensing field 81, while spectrally dispersed image 68 reflects both the position and spectral wavelengths of each signal within the spectra generated by beads 64. Using an accurately calibrated system, analyzer 90 can determine the absolute wavelengths of a particular dispersed image 96a by identifying the associated bead position 64a, particularly where beads 64 do not overlap along the y-axis. As can be understood with reference to FIGS. 6B and 6C, correlation of beads' locations and spectrally dispersed images 96 may be facilitated by including a calibration signal 40c within at least one of the spectra generated by a bead. Such calibration signals will often be included in at least some of the bead spectra, optionally being included in each bead spectrum. Where the calibration signal wavelength is known, the location of the associated bead along the x-axis can be determined from the location of the calibration signal energy within the dispersed image 68 from the diffracting characteristics of wavelength dispersive element 54.

Figure 7A:
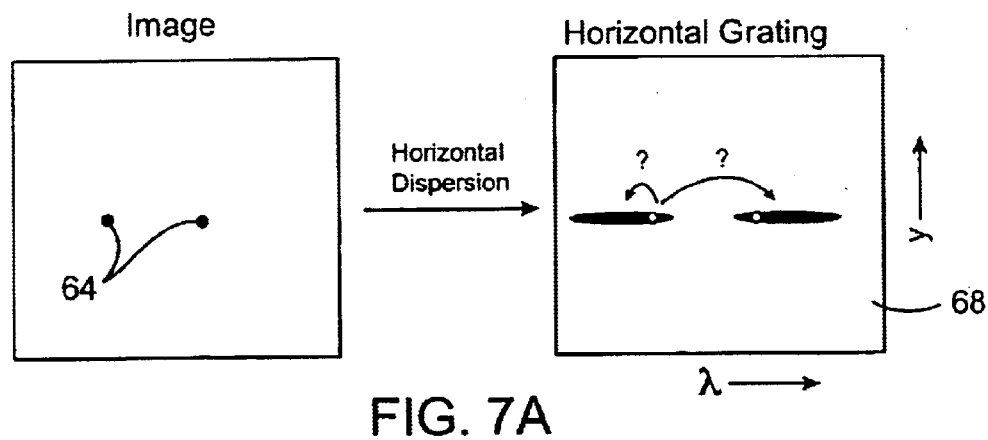
FIGS. 7A–7C schematically illustrate a system and method for resolving ambiguities among overlapping dispersed spectra.
Figure 7B:
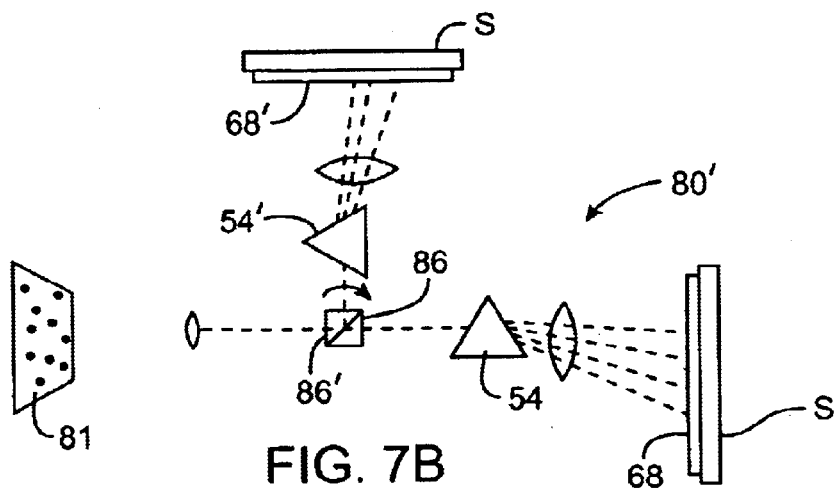
Figure 7C:
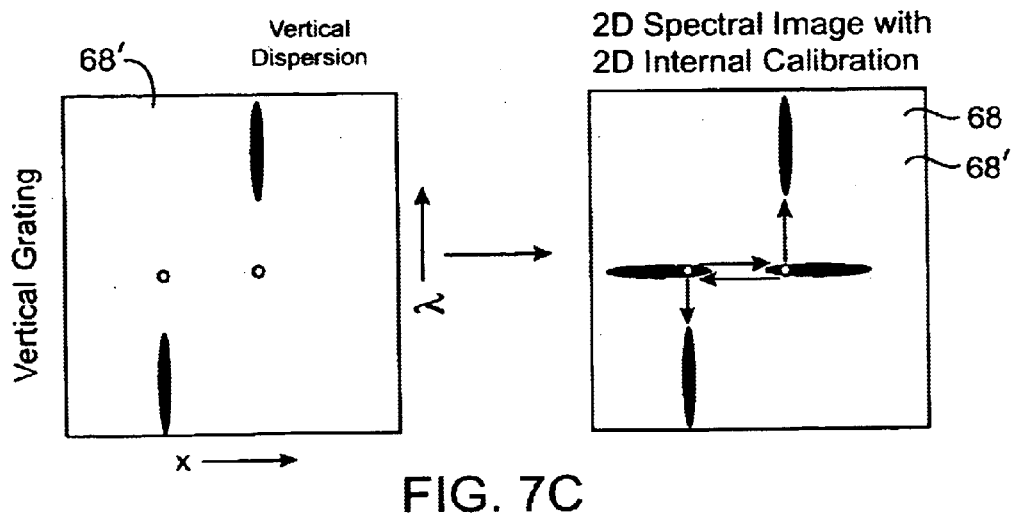

Referring now to FIGS. 7A–7C, ambiguity may arise when images of beads 64 fall along and/or adjacent to a dispersion axis, along a horizontal line in the example of FIG. 7A. To avoid such ambiguity, an alternative two-dimensional spectral sensing system 80' includes an additional beam splitter 86' with a second dispersive element or wavelength dispersive element 54', with the second wavelength dispersive element having a diffraction axis oriented at an angle to the dispersive axis of the first wavelength dispersive element 54 relative to the image of the two-dimensional sensing field 81. Typically, the second wavelength dispersive element will have a dispersive axis oriented at 90° to the dispersive axis of the first wavelength dispersive element, although any angle between 0° and 180° could be used. This second wavelength dispersive element generates a dispersed image 68' along the second dispersive axis (typically orthogonal to the first dispersive axis), allowing analyzer 60 to unambiguously distinguish the spectra from each discrete point within the image. In related embodiments, two orthogonal (or otherwise angularly offset) dispersive elements may be disposed along the same imaging path, or possibly even jowled together to disperse a single image spectrally along two offset dispersive axes. The tow offset spectra may be imaged onto a single sensor. Positions of the beads may be determined from the intersections of each spectral pair, so that a processor derives the position form the combined images 68 and 68', as can be understood with reference to FIG. 7C.

In the preferred embodiment, the original image is split into 2 (or 3) images at ratios that provide more light to the spectrally dispersed images, which have several sources of light loss, than the direct image. In the preferred embodiment, the spectral dispersion is performed using holographic transmission gratings, however, similar results can be obtained using standard reflection gratings.

This system will be useful for any spectral imaging application where the image is made up of discrete points, such as discrete labeled cellular material. It should also be useful for high throughput screening of discrete spectral images such as single molecules or ensembles of molecules immobilized on a substrate such as a surface or bead. This technique can also be used to perform highly parallel reading of spectrally encoded beads.

Varying Signal Strengths

Figure 8:
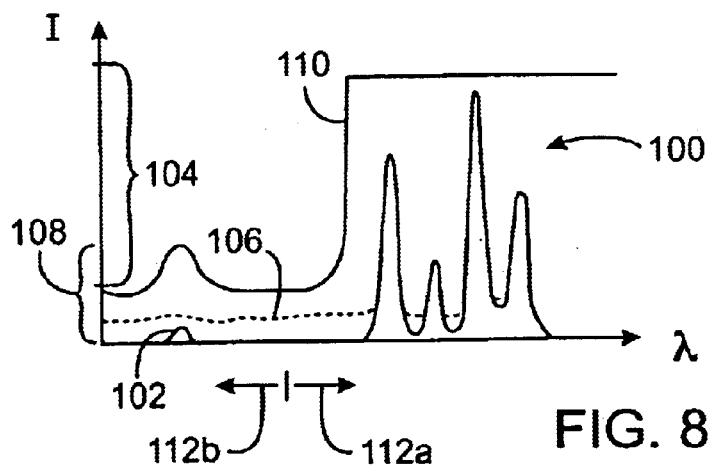
FIGS. 8 and 8A–8C graphically illustrates a wide variation in signal intensities between a spectral label and an assay marker for the exemplary probes illustrated in FIG. 2, and a method for identifying such signals.
Figure 8A:
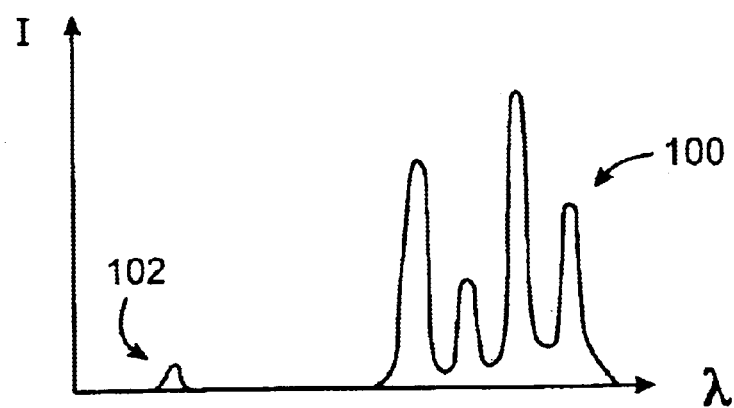

Referring now to FIGS. 2 and 8, test fluid 34 may generate two very different types of signals for interpretation of parallel assays: semiconductor nanocrystals 37 affixed to the bead bodies generate a relatively robust, high intensity label spectra 100, while assay markers 38 may generate a significantly lower intensity assay signal 102. The significant difference in the strengths of these two types of signals may complicate the interpretation of an actual individual spectra from a highly multiplexed assay, such as that illustrated schematically in FIG. 8A.

Since it is relatively trivial to detect arbitrarily large signals, a large dynamic range generally requires detection of as few markers as possible; ideally the detection limit will be a single marker. Since it is possible to detect single molecules and single semiconductor nanocrystals, it should in principle be possible to reach this level of detection in an assay. One problem arises in optimizing the detection of both the spectral code from a bead, which is typically very bright, and the marker signal from the bead, which is typically very dim.

One issue in the detection of very low signal levels is integration time, i.e., how long must a signal be integrated to be detected. In the case of single molecules, the answer is approximately 0.1 to 1.0 second. If it were necessary to scan a point or even a slit across a sample in order to get a two-dimensional spectral image, this could take an extremely long time. Two-dimensional spectral imaging allows one to take spectra from an entire image in the same time that it would take to get a single spectrum. However, to do two-dimensional spectral imaging, the spacing between adjacent beads on the sample should be large enough to limit the overlap of spectra from adjacent beads falling on the CCD detector. Even with precise placement of beads, it is still desirable to devote a large portion of the CCD (and therefore the sample surface) for the spectra of each bead. This means that the density of beads, or other materials, in a two-dimensional spectral image should be fairly low. This reduces the number of beads that can be read simultaneously. The same is true of using multiple slits to scan multiple regions of a sample simultaneously. The spacing between the slits, and therefore the number of regions that can be scanned, is limited by the region of the CCD dedicated to reading the spectra from each slit. Furthermore, in the case of large signals, e.g., for instance the signal from a spectrally encoded bead, the integration time for each image may be less than the readout rate of the CCD. In that case, the advantage of two-dimensional spectral imaging is lost, because the readout time increases linearly with the number of pixels, and thus with the number of beads being detected. It is only when the integration time is long relative to the readout rate that this type of parallel imaging becomes valuable.

An alternative form of spectral imaging is scanning a single slit over the sample and creating a spectral image by plotting spectra as a function of position. In this case, when the integration time is less than the readout rate, the time required to get a complete spectral image is the same as with two-dimensional spectral imaging. When the integration time is longer than the readout rate, however, this method is considerably slower. While slit scanning can never be faster than two-dimensional spectral imaging, it does have the added advantage that high density samples can be used, since no portion of the CCD and sample must be devoted to spectra.

As described above, there are different approaches for spectral imaging. The appropriate choice depends on the integration time required to collect signal from the bead. For very short integration times needed for, e.g., spectral code reading, a scanned slit is preferred. For long integration times, e.g., for marker reading, two-dimensional spectral imaging is most appropriate. Since the above described encoded beads include an assay marker associated therewith, both long and short integration time acquisitions would be beneficial. It would therefore be desirable to develop a system that can maximize simultaneously the detection speed of both short and long integration time signals.

Figure 8B:
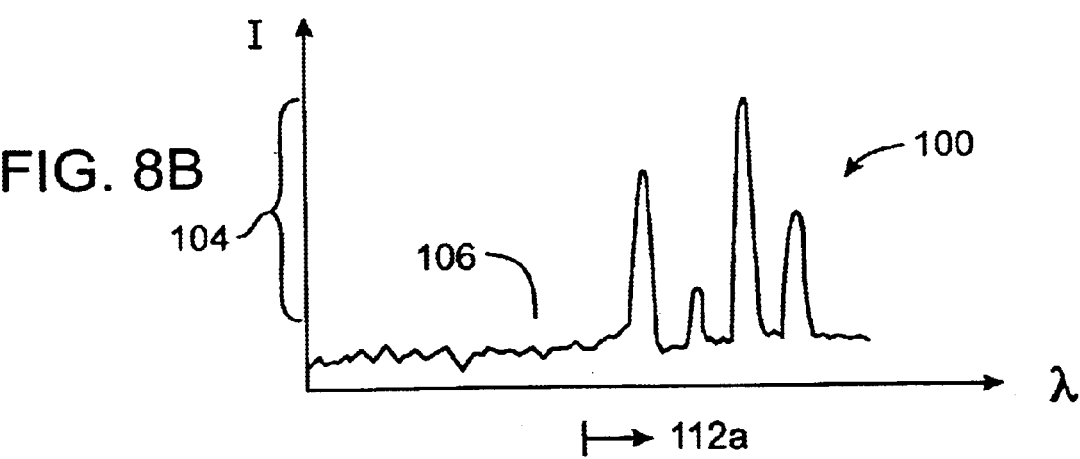
Figure 8C:
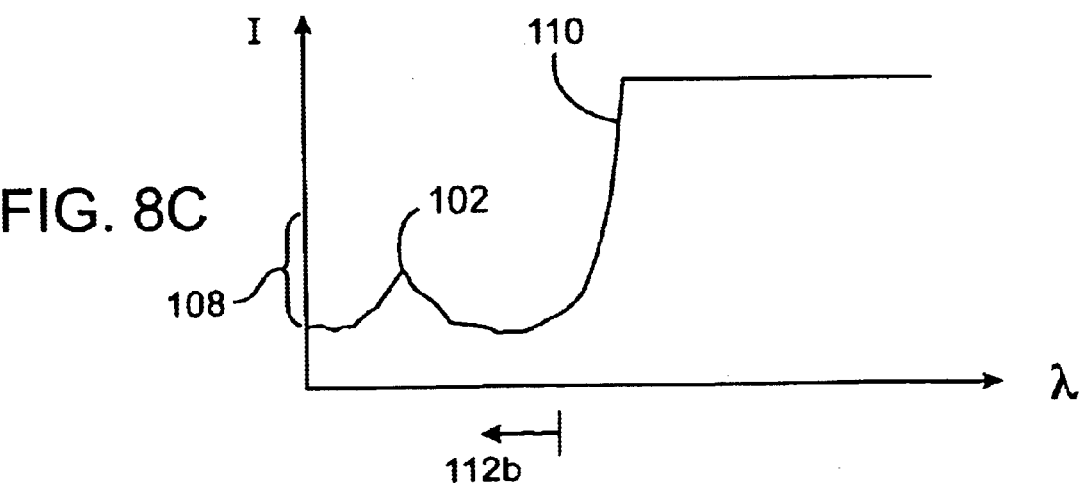

Referring to FIGS. 8 and 8B, a relatively short integration time, such as that provided by a scanning system, might provide a first dynamic range 104. Unfortunately, a scanning system having dynamic range 104 may exhibit a background noise level 106 which makes interpretation of assay signal 102 problematic. Alternatively, as shown in FIGS. 8 and 8C, a reading system which could efficiently gather information despite a relatively long integration time, so as to provide a lower intensity dynamic range 108 appropriate for reading assay signal 102, may exhibit saturation (schematically illustrated as the flat region of long-integration measured signal 110) induced by the relatively high-intensity label spectra. In many embodiments, overcoming these potentially conflicting criteria is facilitated by maintaining the label spectra within a first wavelength range 112a, and the assay marker signals within a second wavelength range 112b which is separate from the first wavelength range.

Figure 9:
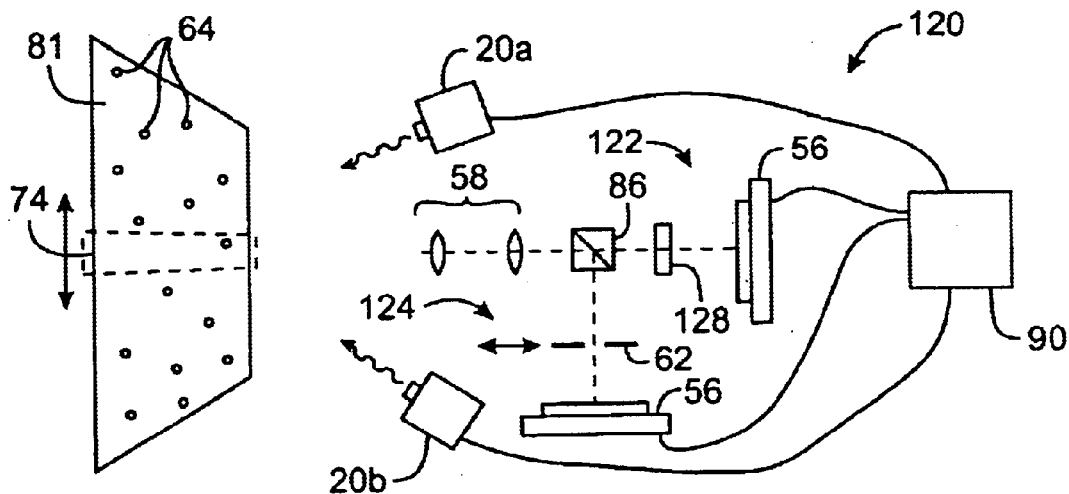
FIG. 9 schematically illustrates a system and method for simultaneously imaging a plurality of assay markers, and for sequentially scanning associated spectral labels for a plurality of spectrally encoded assay probes, and also illustrates the use of differing excitation energy sources for selectively energizing the assay markers.

FIG. 9 schematically illustrates a technique designed to maximize the rate of decoding and reading the markers from spectrally encoded beads. It involves both slit scanning and two-dimensional imaging. In this system, beads 64 are scanned rapidly under a slit (by movement of the beads and/or scanning of the slit). During this time, the spectral codes are read at a rate that is fast relative to the read-out rate of the CCD detector. After the beads pass the slit or are scanned, they may move into an imaging area. Once the image area has been filled, the scanning stops and a single image is taken of the beads. The image is passed though a band-pass filter 128 that selects only the signal from the marker. This image is acquired on a two-dimensional array. The spectral codes from the scanned slit are then correlated with the two-dimensional image to combine the code and marker data. Once completed, a new sample of beads is scanned past the slit and into the image area and the process is repeated. Alternatively, two-dimensional imaging may occur before or during scanning and/or the scanning and imaging may be performed in the same static viewing area, as shown.

With this system, it is possible to maximize the acquisition efficiency of both types of signals. As an example, a set of brightly encoded beads may generate low intensity marker signals. For this example, it is assumed that: (1) the spectral code can he read with an integration time of 10 ms and the marker can be read with an integration time of 1 second; and (2) that it takes 100 steps to scan a slit across the entire image and that the spacing between multiple, adjacently scanned slits may be 20% of the image size. To acquire a spectral image using slit scanning, the integration time at each position might be 1 second to detect both the code and the marker. Therefore, the total acquisition time for a single image would be 100 seconds. To use two-dimensional spectral imaging, the scanning rate is increased; however, the density of the sample scanned is decreased. This might reduce the number of beads per image by a factor of 20. While the two-dimensional spectral image can then be acquired in 1 second, 20 such areas should be scanned to accumulate the same data as in the single slit scanning example. Therefore, the data is acquired in 20 seconds. One final disadvantage of using the two-dimensional spectral imaging system is that the signal from the spectral code should not saturate in the time required to detect the marker.

By using the combination scanning/imaging system described herein, the acquisition time is greatly reduced. The spectral codes are read at 10 ms/step over 100 steps. The marker image is detected with a single 1-second integration time. The total acquisition time is then 2 seconds for the whole spectral image.

Referring to FIGS. 8 and 9, a scanning/imaging system 120 generally comprises a detector which is optically coupled with two-dimensional sensing field 81 by optics 58, and a scanner 124 having an aperture 62. Aperture 62 will generally be movable relative to bead 64 of two-dimensional sensing field 81, either through movement of the aperture (and associated apertured sensing field 74), by software coupled to the CCD, or movement of the beads.

To allow scanning/imaging system 120 to detect relatively low-intensity signals within the two-dimensional sensing field 81, optics 58 image the sensing field upon a surface 122 of sensor 56. A spectral filter 128 selectively transmits marker signals 102 to sensor 56 of the detector, thereby avoiding saturation from the relatively high-intensity spectral label signals. Using our simple marker/label separation scheme illustrated in FIG. 8, filter 128 may comprise a dichroic filter which selectively transmits the marker signals within second range 112b. Clearly, more complex filtering and signal separation arrangements are possible. Regardless, as numerous beads 64 within two-dimensional sensing field 81 can have their assay markers detected simultaneously, a relatively long integration time may be employed without adding excessively to the overall sensing time.

In the schematic embodiment illustrated in FIG. 9, a beam splitter 86 directs a separate signal portion to a sensor 56 of scanner 124. Aperture 62 restricts an apertured sensing field of the scanner 74 so that beads 64 are read sequentially in a line. Each reading of the relatively bright spectral codes from the beads can make use of a quite short integration time, optionally during the long integration time employed by the two-dimensional marker imaging system.

In an alternative embodiment, spectra and image/position data may be sensed by the same sensor. Any of the scanning systems described herein may be applied. After the spectra are scanned (or before) a bandpass filter may remove the spectral information, leaving assay signals and bead location information for each associated signal in the 2-D image. Assay results may then be determined from the locations of the signals and the dispersion of the grating.

As mentioned above, sequential sensing of the spectra may be performed by moving the aperture relative to the sensing field, by software, by moving the beads (or other signal sources) relative to the optical train or scanning system, or even by scanning one of an excitation energy or the beads relative to the other. Aperture scanning may be effected by a galvanometer, by a liquid crystal display (LCD) selective transmission arrangement, by other digital arrays, or by a digital micro-mirror array (DMD). Bead scanning systems may use a fluid flow past a slit aperture, with the beads flowing with the fluid. Such bead flow systems result in movement of the aperture relative to the beads, even when the aperture remains fixed, as movement may be determined relative to the bead's frame of reference.

Figure 9A:
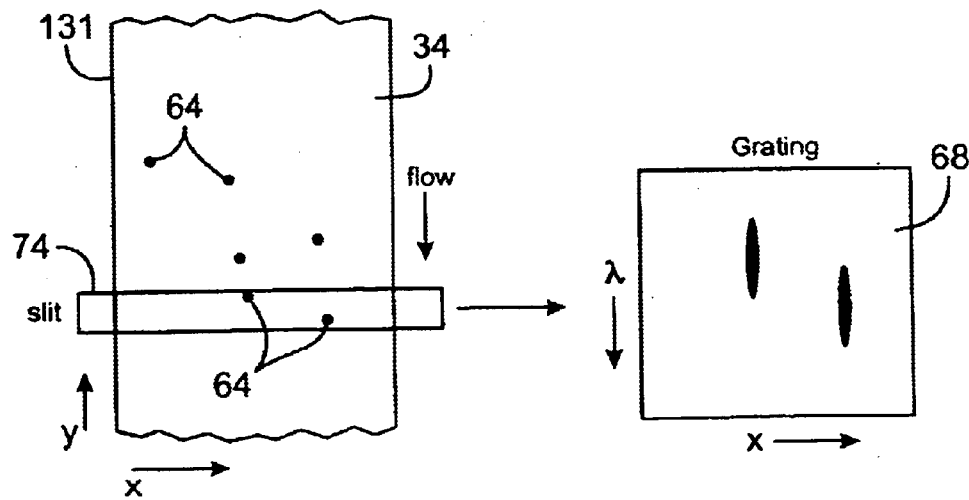
FIG. 9A schematically illustrates a fluid flow assay scanning system and method.

Referring now to FIG. 9A, a simple fluid-flow assay system can make use of many of the structures and methods described herein above. In the illustrated embodiment, a test fluid 34 flows through a channel 131 so that beads 64 move across sensing field 74. Beads 64 within the slit-apertured sensing region are spectrally dispersed and imaged as described above. As the location of the slit-aperture is known, absolute spectral information regarding the label spectra and assay signals may be determined from dispersed image 68. When a plurality of beads are within sensing region 74 but separated along the x axis as shown, multiple beads may be read simultaneously by a CCD, or the like. Flowing of the beads sequentially through sensing region 74 may allow simultaneous assay preparation and reading using flow injection analysis techniques, or the like.

Imaging of sensing region 74 may be facilitated by providing a thin, flat channel 131 so that beads 64 are near opposed major surfaces of the channel, with at least one of the channel surfaces being defined by a material which is transparent to the spectra and marker signals. This fluid-flow system may be combined with many aspects of the systems described hereinabove, for example, by providing two different energy sources for the label spectra and assay markers, by areal imaging of beads 64 distributed throughout a two-dimensional sensing region adjacent to or overlapping with slit-apertured sensing region 74, and the like.

A variety of modifications of the scanning/imaging system 120, and of the other imaging systems described herein above, are encompassed within the present invention. For example, the optics schematically illustrated in the figures may include optical elements along the optical path before any apertures, after any apertures, and/or on either side of any apertures. Similarly, at least a portion of the optical train may be disposed after any beam splitters. Rather than relying on separate sensors 56 for scanning, position indication, two-dimensional imaging, and/or diffraction image sensing, the optics may be arranged so as to direct these differing images to a common sensor. Differing images may also be acquired simultaneously or sequentially. Where areal sensing is not required, it may be possible to make use of linear, point, or bulk light sensors or photodetectors.

The systems of the present invention are particularly well-suited for identification of label spectra that are spatially intermingled with other markers, especially where at least one label and/or at least one assay marker comprises a semiconductor nanocrystal. As described above, an analyzer 90 will often correlate the labels from each bead with an associated marker signal (which may comprise an absence or absorbance of energy having a characteristic wavelengths, scattering, a change in signal/energy characteristics, or the like).

In one preferred embodiment, the two detection pathways follow the same optical path and fall on the same detector. In this embodiment, the excitation of the sample under the slit is shuttered during image acquisition or is otherwise oriented such that no spectra are obtained during the image acquisition. In separate embodiments, the multiple detection pathways can be used as well as multiple detectors.

The scanning/imaging system of FIG. 9 illustrates yet another advantageous aspect of the present invention which may find applications in other signal detection systems including those described above. A simplified system for sensing both high-intensity signals (such as spectral labels) and normally low-intensity signals (such as assay markers) may include a first excitation energy source 20a transmitting an excitation energy toward fluid 34 (see FIG. 1) for generation of spectral codes from the beads. First excitation energy source 20a may also, at least to some extent, induce marker signals 102. However, a second excitation energy source 20b also transmits an excitation energy source toward the beads, with the excitation energy from this second source selectively energizing the assay markers. This may be accomplished, for example, by limiting the second excitation energy source to a wavelength that is higher in energy than the low-intensity marker signals, but which is lower in energy than the high-intensity label signals. By selectively energizing the first and/or second excitation energy sources, and/or by varying at least one of the excitation energies relative to the other, the dynamic range of the overall system can be effectively broadened to accurately and reliably sense both the otherwise relatively weak assay marker signals and the quite strong spectral labels. Either or both of these excitation energy sources might be scanned relative to the beads to effectively control the location and/or size of the sensing field for the labels and/or assay markers.

In many preferred embodiments of signal detection systems, two light sources are used. The first light source is an inexpensive blue light source for exciting the spectral code and the marker simultaneously. The blue source illuminates the slit region of the sample, and the apertured region of the sample is then dispersed and sensed as described above. Since it does not require much light to detect the spectral code, this light source can be very inexpensive. The two-dimensional image region of the sample is then excited with a higher power red laser, which excites only the marker semiconductor nanocrystals. This allows efficient detection of the marker while eliminating the possibility of the spectral codes saturating due to high excitation intensity.

In an alternative embodiment, the two light sources are used to tune the relative intensities of the code and marker during simultaneous detection. For example, if both marker and code are detected using slit scanning or two-dimensional spectral imaging alone, it is likely that the code would saturate in the time required to detect the marker. This is avoided if the relative excitation intensity for the code (blue light) is very weak relative to the excitation intensity for the marker (red light). The advantage of such a setup is that the relative intensity of the code to marker signal can be tuned by adjusting the two light sources. This reduces any concerns about dynamic range limitations between the code and the marker. This two-light source system is advantageous in any detection scheme that involves a wide dynamic range that must be simultaneously detected (such as the marker/bar-code system). It should therefore be useful in systems other than that described in the current disclosure.

Fixed Position Beads

Techniques to analyze bead-based assays can be flow based and/or imaging based. In the flow-based analysis, an instrument such as sheath flow cytometer is used to read the fluorescence and scatter information from each bead individually. Flow methods have the disadvantage of requiring a relatively large volume of sample to fill dead volume in the lines and do not allow averaging or re-analysis of data points. Flow methods do allow a large number of beads to be analyzed from a given sample. Imaging based systems, such as the Biometric Image™ system, scan a surface to find fluorescence signals. Advantages over the flow system include small (<20 microliter) sample volumes and the ability to average data to improve signal to noise. The disadvantage is the need for a large area in order to keep beads separated, and the dependence on beads being an appropriate dilution to ensure that a sufficient number can be analyzed without too many forming into doublets, triplets, or the like.

Figure 10B:
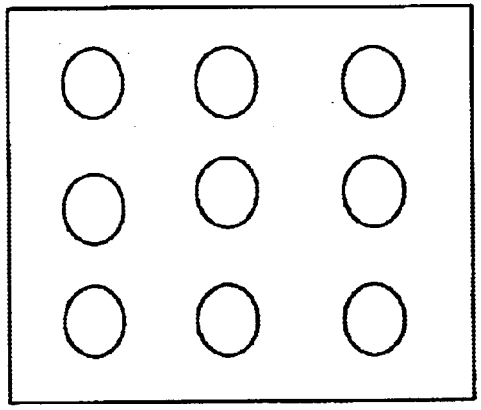
FIGS. 10A–10C schematically illustrate a plate for positioning semiconductor nanocrystal assay probes, together with a method for the use of positioned probes in multiplexed assays.
Figure 10A:
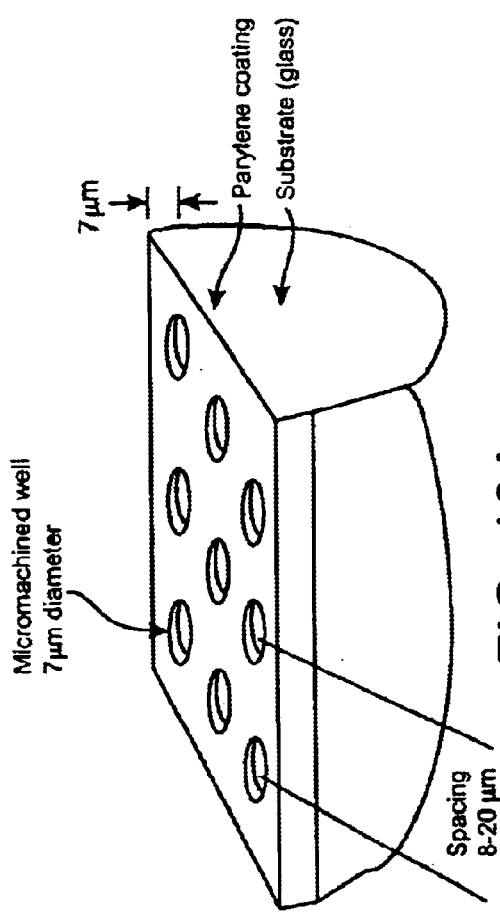
Figure 10C:
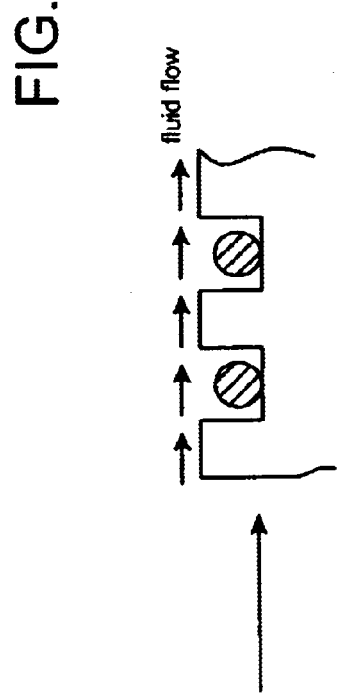
Figure 10C:
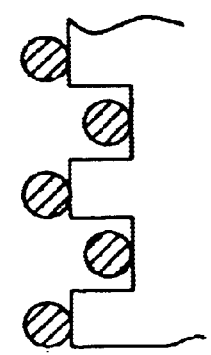

Referring now to FIGS. 10A–10C, beads can be immobilized on a planar surface such that they are regularly spaced in a chosen geometry. The beads can be immobilized by micromachining wells into the planar surface. For example, 7-micron wells that are 7 microns deep, can be created by ablating a 7 micron layer of parylene on a glass surface using a focused laser. Other methods can be used to create microstructures on the glass surface that behave as wells. The well dimensions are chosen such that only a single bead is captured in the well and such that, when a lateral flow of fluid passes the beads, the single beads remain trapped in the wells (see FIG. 10C). The 7-micron well described may be suitable for analysis of beads from around 4 microns to 6 microns, or "monodisperse" 5 micron beads. Other methods for capturing beads include selective deposition of polymers using light-activated polymerization, where the pattern of light is determined using a photoresist. The polymers then bind non-specifically to single beads and other beads can be washed away.

In use, the mixture of spectrally encoded beads that have undergone an assay are deposited onto the capture surface and allowed to settle into wells (by gravity) or to bind to the capture surface. Excess beads are then washed away leaving single beads filling up some portion, for example, >90% of the wells or capture positions.

Still further structures might be used to immobilize and/or position the beads, including superparamagnetic bead positioners being developed by IMMUNICON CORPORATION of Pennsylvania, and by ILLUMINA, INC. of San Diego, Calif.

The captured beads can then be analyzed using an imaging system to capture fluorescence data at various emission wavelengths for each bead. This method provides advantages over a simple scan of randomly placed beads because (1) beads are known to be separated so the spatial resolution required for detection can be reduced as doublets do not have to be found and rejected—this leads to greater analysis efficiency, (2) the packing of beads can be considerably higher while still retaining spatially separated singlet beads, (3) the beads do not move relative to the support and so can be scanned multiple times without concerns about movement, and (4) the concentration of beads in the sample that is applied does not need to be precise (in the random scattering approach too high a concentration leads to a high packing and eventually a multi-layer structure whereas too low a concentration leads to too few beads being analyzed).

Figure 11:
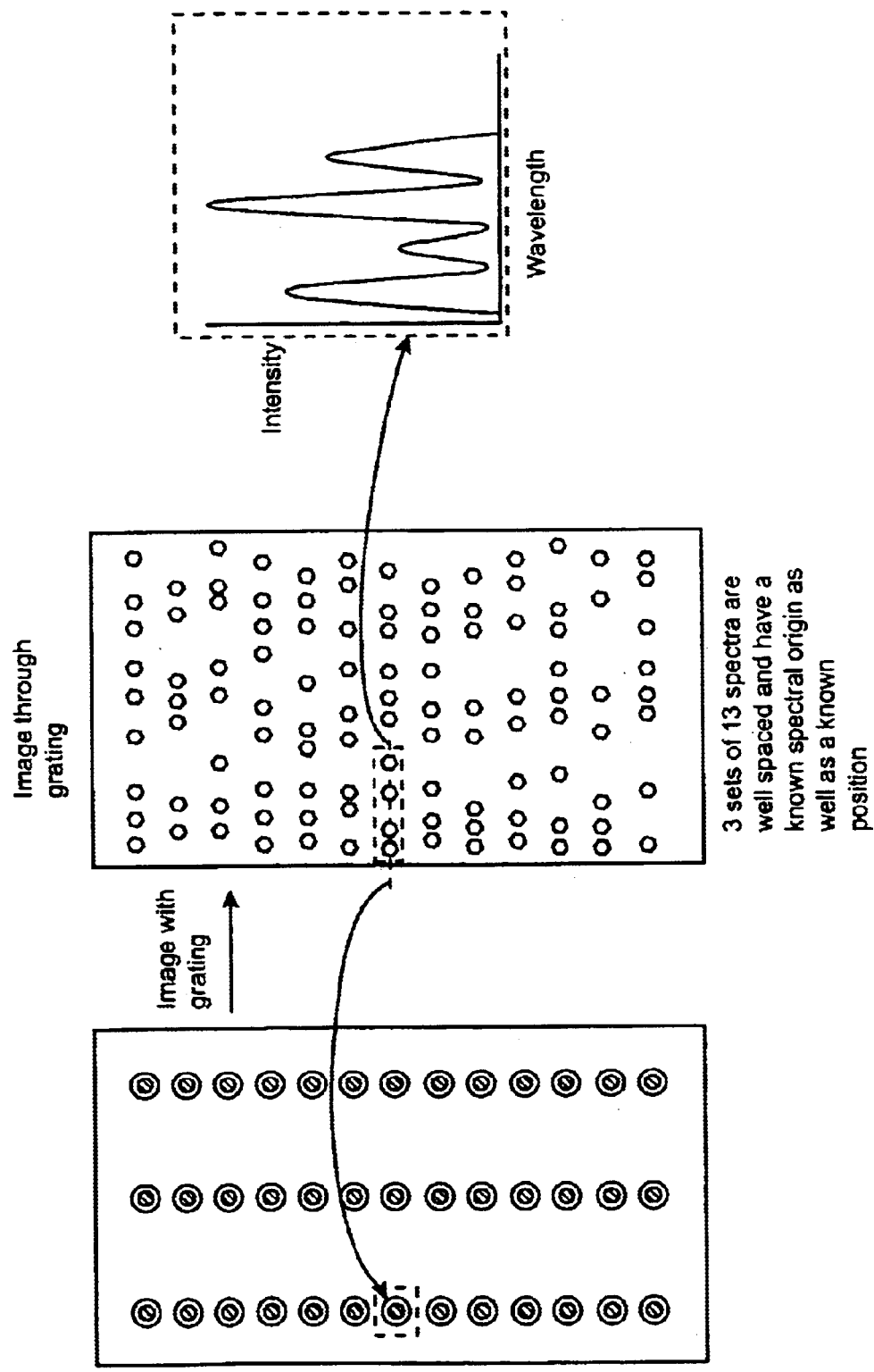
FIG. 11 schematically illustrates a method for reading the spectral labels and/or identifying assay results using the probe positioning plate of FIG. 10C.

In a system where spatial and spectral information are combined by placing a coarse grating (reflection or transmission) in the emission path, such that the emitted light from each bead is spectrally dispersed in one dimension, the use of micromachined wells is particularly useful. The wells are machined such that the dispersed images of each bead cannot overlap. In addition, knowledge of the bead positions means that absolute wavelength determination can be carried out rather than relative determinations or using a spectral calibrator (See FIG. 11).

Still further alternative bead positioning means are possible. In one variation of the positioning wells illustrated in FIGS. 10A–10C, a closely packed array of collimated holes may be distributed across a surface. Where the holes extend through a substrate defining the surface, a pressure system may be provided along an opposed surface so as to actively pull beads 64 and test fluid 32 into the array of holes. Such a system would allow a set of beads to be pulled into positioning wells, to have the assay results (optionally including bead labels and assay markers) read from the entrained beads, and then optionally, to push the beads out of the through holes. Such a positioning and reading cycle may be repeated many times to read a large number of beads within a test fluid. While there may be difficulty in transporting the beads and test fluid to the positioning surface, such a system has significant advantages.

Specific structures for containing test fluids with beads, and/or for directing flows of such fluids and beads, may improve spectral code reading performance. Codes may be read from above, from below, or from an angle relative to vertical. Reading codes from below, for example, may be enhanced by using a fluid containing body with an opaque material over the fluid. The fluid surrounding the beads may have an index of refraction which substantially matches that of the material of the lower portion of the fluid containing body. Such structures may be particularly beneficial when reading dense bead codes.

While the exemplary embodiments of the present inventions have been described in some detail for clarity of understanding, a variety of modifications, adaptations, and changes will be obvious to those of skill in the art. Hence, the scope of the present invention is limited solely by the appended claims.

What is claimed is:

1. A system comprising:
   a plurality of spatially resolved labels generating identifiable spectra in response to excitation energy, wherein at least some of the spectra comprise a plurality of signals for each label, the plurality of signals defining a plurality of wavelengths, the wavelengths from the spectra being intermingled;
   a first family of the labels generating different identifiable spectra having first signals with a first wavelength, a first label of the first family including an associated second signal defining a second wavelength, a plurality of labels of the first family including associated second signals having wavelengths which are different than the second wavelength; and
   a detector simultaneously imaging the spectra of the plurality of spatially resolved labels upon a surface for identification of the labels.

2. The system of claim 1, wherein the labels comprise at least one semiconductor nanocrystal.

3. The system of claim 1, wherein each label comprises at least one population of semiconductor nanocrystals, each population generating a signal having a population wavelength in response to the excitation energy.

4. The system of claim 3, wherein at least some of the labels comprise a plurality of the populations supported by a matrix.

5. The system of claim 1, further comprising at least one probe body including a label and an associated assay indicator marker, the indicator markers generating indicator signals in response to an interaction between the probe body and an associated test substance so as to indicate results of an assay.

6. The system of claim 1, wherein the simultaneously imaged labels are distributed across a two-dimensional sensing field.

7. The system of claim 6, wherein the detector comprises a diffractor and a sensor, and wherein each label is sufficiently smaller than the sensing field so that the spectra can be wavelength-dispersed by the diffractor without excessive overlap of the dispersed spectra upon the sensor.

8. The system of claim 6, wherein the detector comprises a light sensor and a diffractor, the diffractor disposed between the sensing field and the light sensor, the sensor simultaneously sensing the spectra from the plurality of labels.

9. The system of claim 8, wherein an open optical path extends from the sensing field to the diffractor and from the diffractor to the sensor, the sensor comprising an areal sensor and having the surface, the open optical path having an open cross-section with significant first and second open orthogonal dimensions.

10. The system of claim 9, wherein no slit aperture is disposed along the optical path to restrict the sensing field, and wherein the diffractor comprises an element selected from the group consisting of a prism, a dispersive reflective grating, and a dispersive transmission grating.

11. The system of claim 1, further comprising a spatial position indicator to identify label positions within a sensor field of the detector, wherein the detector senses relative spectral data.

12. The system of claim 11, further comprising a spectral analyzer coupled to the label position indicator and the detector, the analyzer deriving absolute wavelengths of the spectra in response to the relative spectral data and the identified label positions.

13. The system of claim 12, further comprising a first beam splitter disposed to optically couple the label position indicator with the sensing filed along a positioning optical path, and to optically couple the detector with the sensing field along a spectral optical path.

14. The system of claim 13, wherein the detector comprises an areal sensor and wherein the label position indicator comprises a processing module, the first beam splitter directing a first energy from the sensing field, past a diffractor and toward the areal sensor for generating spectral data, the first beam splitter directing a second energy from the sensing field to a position indicator for generation of position data.

15. The system of claim 12, further comprising a second beam splitter disposed along an optical path from the sensing field, wherein a first dispersion member is disposed in the spectral optical path so as to disperse wavelengths of the spectra along a first axis, and wherein a second dispersion member is optically coupled to the second beam splitter so as to disperse wavelengths of the spectra along a second axis, the first axis at an angle to the second axis relative to the sensing field for resolving spectral ambiguities of overlapping wavelengths along the first axis.

16. The system of claim 1 wherein the detector comprises means for distributing the signals across a sensor in response to wavelengths of the signals and positions of the labels in a sensor field, the distributing means disposed between the sensing field and the sensor.

17. The system of claim 16, further comprising means for determining positions of the labels within the sensing field, and a spectral analyzer coupled to the positioning means and the sensor, the analyzer determining the spectra.

18. The system of claim 17, wherein the positioning means comprises either an areal sensor and a beam splitter, or a calibration reference signal within the at least some spectra.

19. A system comprising:
a plurality of spatially resolved labels generating identifiable spectra in response to excitation energy, wherein at least some of the spectra comprise a plurality of signals for each label, a first family of the labels generating different identifiable spectra having first signals with a first wavelength, a first label of the first family including an associated second signal defining a second wavelength, a plurality of labels of the first family including associated second signals having wavelengths which are different than the second wavelength;
a detector simultaneously imaging the spectra of the plurality of spatially resolved labels upon a surface of a sensor, the detector comprising a dispersion member dispersing wavelengths of the spectra across the surface of the sensor; and
a spatial position indicator to identify label positions within a sensor field of the detector.

20. A system comprising:
a plurality of spatially resolved labels generating identifiable spectra in response to excitation energy, at least some of the spectra having a plurality of wavelengths, at least some of the labels being distributed in two dimensions across a two-dimensional sensing field;
a detector comprising a light sensor having a two-dimensional light sensor surface, an open optical path, and a diffractor, the optical path of the detector optically coupling the sensor surface to the sensing field, the optical path sufficiently open in two orthogonal cross-sectional dimensions that spectra from the plurality of spatially resolved labels in the sensing field are simultaneously imaged upon the surface of the sensor with the simultaneously imaged spectra distributed in two dimensions across the sensor surface, the diffractor disposed along the optical path between the sensing field and the light sensor; and
an analyzer coupled to the detector, the analyzer identifying the labels in response to the simultaneously sensed spectra.

21. The system of claim 19, wherein the labels comprise at least one semiconductor nanocrystal.

22. The system of claim 19, wherein each label comprises at least one population of semiconductor nanocrystals, each population generating a signal having a population wavelength in response to the excitation energy.

23. The system of claim 22, wherein at least some of the labels comprise a plurality of the populations supported by a matrix.

24. The system of claim 19, further comprising at least one probe body including a label and an associated assay indicator marker, the indicator markers generating indicator signals in response to an interaction between the probe body and an associated test substance so as to indicate results of an assay.

25. The system of claim 19, wherein the simultaneously imaged labels are distributed across a two-dimensional sensing field.

26. The system of claim 25, wherein the detector comprises a diffractor and a sensor, and wherein each label is sufficiently smaller than the sensing field so that the spectra can be wavelength-dispersed by the diffractor without excessive overlap of the dispersed spectra upon the sensor.

27. The system of claim 25, wherein the detector comprises a light sensor and a diffractor, the diffractor disposed between the sensing field and the light sensor, the sensor simultaneously sensing the spectra from the plurality of labels.

28. The system of claim 27, wherein an open optical path extends from the sensing field to the diffractor and from the diffractor to the sensor, the sensor comprising an areal sensor and having the surface, the open optical path having an open cross-section with significant first and second open orthogonal dimensions.

29. The system of claim 20, wherein a slit aperture is not disposed along the optical path to restrict the sensing field, and wherein the diffractor comprises an element selected from the group consisting of a prism, a dispersive reflective grating, and a dispersive transmission grating.

30. The system of claim 19, further comprising a spectral analyzer coupled to the label position indicator and the detector, the analyzer deriving absolute wavelengths of the spectra in response to the relative spectral data and the identified label positions.

31. The system of claim 30, further comprising a first beam splitter disposed to optically couple the label position indicator with the sensing filed along a positioning optical path, and to optically couple the detector with the sensing field along a spectral optical path.

32. The system of claim 31, wherein the detector comprises an areal sensor and wherein the label position indicator comprises a processing module, the first beam splitter directing a first energy from the sensing field, past a diffractor and toward the areal sensor for generating spectral data, the first beam splitter directing a second energy from the sensing field to a position indicator for generation of position data.

33. The system of claim 31, further comprising a second beam splitter disposed along an optical path from the sensing field, wherein a first dispersion member is disposed in the spectral optical path so as to disperse wavelengths of the spectra along a first axis, and wherein a second dispersion member is optically coupled to the second beam splitter so as to disperse wavelengths of the spectra along a second axis, the first axis at an angle to the second axis relative to the sensing field for resolving spectral ambiguities of overlapping wavelengths along the first axis.

34. The system of claim 19, wherein the detector comprises means for distributing the signals across a sensor in response to wavelengths of the signals and positions of the labels in a sensor field, the distributing means disposed between the sensing field and the sensor.

35. The system of claim 34, further comprising means for determining positions of the labels within the sensing field, and a spectral analyzer coupled to the positioning means and the sensor, the analyzer determining the spectra.

36. The system of claim 35, wherein the positioning means comprises either an areal sensor and a beam splitter, or a calibration reference signal within the at least some spectra.

* * * * *